US006908618B2

(12) United States Patent
Samal

(10) Patent No.: US 6,908,618 B2
(45) Date of Patent: Jun. 21, 2005

(54) PRODUCTION OF NOVEL BOVINE RESPIRATORY SYNCYTIAL VIRUSES FROM CDNAS

(75) Inventor: Siba K. Samal, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 10/187,790

(22) Filed: Jul. 3, 2002

(65) Prior Publication Data

US 2003/0065158 A1 Apr. 3, 2003

Related U.S. Application Data

(63) Continuation-in-part of application No. 09/554,131, filed as application No. PCT/US98/23231 on Nov. 9, 1998, now abandoned.

(60) Provisional application No. 60/064,091, filed on Nov. 10, 1997.

(51) Int. Cl.$^7$ .............................................. A61K 39/155

(52) U.S. Cl. ................................ 424/211.1; 424/199.1; 424/204.1; 424/205.1; 435/91.51; 514/44

(58) Field of Search ........................... 424/204.1, 205.1, 424/211.1, 199.1; 435/69.3, 236, 91.51; 514/44

(56) References Cited

U.S. PATENT DOCUMENTS

| | | | | |
|---|---|---|---|---|
| 5,716,821 A | 2/1998 | Wertz et al. | ............. | 435/235.1 |
| 5,733,555 A | 3/1998 | Chu | ........................ | 424/211.1 |
| 5,840,520 A | 11/1998 | Clarke et al. | .............. | 435/69.1 |
| 5,993,824 A | 11/1999 | Murphy et al. | .......... | 424/211.1 |

FOREIGN PATENT DOCUMENTS

| | | |
|---|---|---|
| WO | WO 92/01471 | 2/1992 |
| WO | WO 92/07940 | 5/1992 |

OTHER PUBLICATIONS

Khattar, S. et al., "Deletion and Substitution Analysis Defines Regions and Residues within the Phosphoprotein of Bovine Respiratory Syncytial Virus That Affect Transcription, RNA Replication, and Interaction with the Nucleoprotein", Virology, 2001, pp. 253–269.

Khattar, S. et al., "Mutational Analysis of the Bovine Respiratory Syncytial Virus Nucleocapsid Protein Using a Minigenome system: Mutations That Affect Encapsidation, RNA Synthesis, and Interaction with the Phosphoprotein", Virology, vol. 270, 2000, pp. 215–228.

Khattar, S. et al., "Mapping the domains on the phosphoprotein of bovine respiratory synctial virus required for N–P and P–L interactions using a minigenome system", J. General Virology, 2001, vol. 82, pp. 775–779.

Yunus, A. et al., "Resuce of Bovine Respiratory Syncytial Virus from Cloned cDNA: Entire Genome Sequence of BRSV Strain A51908", Virus Genes, 2001; 23:2, pp. 157–164.

Juhasz et al. "The temperature sensitive (ts) phenotype of a cold–passaged (cp) live attenuated respiratory syncytial virus vaccine candidate, designated cpts530, results from a single amino acid substitution in the L protein", 1997, J. Virology, vol. 71, No. 8; pp. 5814–5819.

Fields et al. 1996. Virology, Third edition. Lippencott–Raven Publishers. vol. 1, pp. 1314–1315 and 1322–1323.

*Primary Examiner*—Laurie A. Scheiner
(74) *Attorney, Agent, or Firm*—Arent Fox, PLLC.

(57) ABSTRACT

A method of producing an attenuated bovine respiratory syncytial virus (BRSV) having increased or decreased transcription and/or replication, as compared to a wild-type BRSV, including the steps of inserting a synthetic cDNA which codes for an infectious BRSV into a host cell, wherein the cDNA is operably-linked to a promoter; expressing the cDNA in the host cell to produce the infectious BRSV; and thereafter introducing at least one site-specific RNA point mutation on the P gene of the BRSV. An attenuated BRSV and vaccine produced by the method are also included.

13 Claims, 12 Drawing Sheets

```
HRSV  leader    3'   UGCGC UUU UUUACGCAUGUUGUUUGAACGUAUUUGGUUUUUUUA-CCCCGUUUA  44
                     ****************  *******  ** * *   * ***** **
BRSV  leader    3'   UGCGCUUUUUUACGCAUAUUGUUUGGACAUGUAGGUUUUUUCUAGCCCCGUUUA  45
                                                                 NSIgene start

HRSV trailer 5' ACGAG AAAAAAGUGUCAAAAACUAAUAUCUCGUAAUUUAGUUAAUACACAUAUAAACCAAUUAGAUUAGGGUUUAAA-  -78
                 ************ **********   *** * **  **      * * *     **** *  *  **  * ***
BRSV trailer 5' ACGAGAAAAAAAGUAUCAAAAACUAUCCUCUUGCAACAUAAAGGACAUAUUCUCGUACCAUUAAAUUUUUGAUUUUCUGG -80

HRSV trailer  UUUAUUCCUCCAAGAUUAAAAUGAUAACUUUAGGAUUAGUUCACUA--AAAGUUAUUUAAAAAAUUAUAU-GAU--UUUUAA 3'-155
               ***   **  *  *  *  ***   * ***         *   *   *  **  *  *  * ** ******** ***  *  *  *
BRSV trailer  UUUAGAUCUUGACCAGUGGAAUUUGAGCUUGGAACACAGAUAUGUGGGAAUUUAAGAUUAACAACUAUAUAGAUAAUGUGAG 3'-162
```

Fig. 5

SEQUENCE LISTING

```
<160> NUMBER OF SEQ ID NOS: 18

<210> SEQ ID NO 1
<211> LENGTH: 12
<212> TYPE: RNA
<213> ORGANISM: Bovine respiratory syncytial virus

<400> SEQUENCE: 1

ucaauaauuu uu                                                          12


<210> SEQ ID NO 2
<211> LENGTH: 11
<212> TYPE: RNA
<213> ORGANISM: Bovine respiratory syncytial virus

<400> SEQUENCE: 2

ugcucucagg g                                                           11


<210> SEQ ID NO 3
<211> LENGTH: 53
<212> TYPE: RNA
<213> ORGANISM: Human respiratory syncytial virus

<400> SEQUENCE: 3

auuugcccca uuuuuuuggu uuaugcaagu uuguuguacg cauuuuuucg cgu             53


<210> SEQ ID NO 4
<211> LENGTH: 54
<212> TYPE: RNA
<213> ORGANISM: Bovine respiratory syncytial virus

<400> SEQUENCE: 4

auuugccccg aucuuuuuug gauguacagg uuuguuauac gcauuuuuuc gcgu            54


<210> SEQ ID NO 5
<211> LENGTH: 155
<212> TYPE: RNA
<213> ORGANISM: Human respiratory syncytial virus

<400> SEQUENCE: 5

acgagaaaaa aagugucaaa aacuaauauc ucguaauuua guuaauacac auauaaacca      60

auuagauuag gguuuaaauu uauuccucca agauuaaaau gauaacuuua ggauuaguuc     120

acuaaaaguu auuuaaaaaa uuauaugauu uuuaa                                155
```

-continued

<210> SEQ ID NO 6
<211> LENGTH: 162
<212> TYPE: RNA
<213> ORGANISM: Bovine respiratory syncytial virus

<400> SEQUENCE: 6
acgagaaaaa aaguaucaaa aacuauccuc uugcaacaua aaggacauau ucucguacca 60
uuaaauuuuu gauuuucugg uuuagaucuu gaccagugga auuugagcuu ggaacacaga 120
uaugugggaa uuuaagauua acaacuauau agauaaugug ag 162

<210> SEQ ID NO 7
<211> LENGTH: 54
<212> TYPE: RNA
<213> ORGANISM: Bovine respiratory syncytial virus

<400> SEQUENCE: 7
auuugccccg aucuuuuuug gauguacagg uuuguuauac gcauuuuuuc gcgu 54

<210> SEQ ID NO 8
<211> LENGTH: 52
<212> TYPE: RNA
<213> ORGANISM: Bovine respiratory syncytial virus

<400> SEQUENCE: 8
acgagaaaaa aaguaucaaa aacuauccuc uugcaacaua aaggacauau uc 52

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide used in the construction of cDNA,
encoding BRSV-CAT-F-M2

<400> SEQUENCE: 9
agttattaaa aa 12

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide used in the construction of cDNA,
encoding BRSV-CAT-F-M2

<400> SEQUENCE: 10
gggacaaaat 10

<210> SEQ ID NO 11
<211> LENGTH: 77
<212> TYPE: DNA
<213> ORGANISM: Artificial Sequence
<220> FEATURE:
<223> OTHER INFORMATION: Description of Artificial Sequence: Synthetic
DNA marker

<400> SEQUENCE: 11
agtaattaaa aaaggaccag gtttgaaaca aaacaaggta gagataacaa caaacaaaaa 60
tgaaatgtgg ggcaaat 77

-continued

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic DNA marker

<400> SEQUENCE: 12
agataaataa aaattatgaa agtcaataaa gattatgtgg ggtaaat 47

<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: Synthetic DNA marker

<400> SEQUENCE: 13
agttatataa aagtattata ttaatctcaa agaatcaacc tatttaataa ccaatcattc 60
aaaagatggg gcaaat 76

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic DNA marker

<400> SEQUENCE: 14
ctctttctaa ccccacttcc tatatattga ctagtataca aaaatctaaa tttacagaa 59

<210> SEQ ID NO 15
<211> LENGTH: 726
<212> TYPE: RNA
<213> ORGANISM: Bovine respiratory syncytial virus

<400> SEQUENCE: 15
auggaaaaau uugcaccuga guuucaugga gaagaugcca auacaaaagc aaccaaguuu 60
cuugaauccc uaaaagggaa auuuacuucu ucuaaggauu cuaggaaaaa agauaguaua 120
auaucaguua auuccguaga cauagaauua ccuaaagaga guccuauaac aucuaccaau 180
caaaauauca accaaccaag ugagaucaau gacacuauug cuacaaauca aguucauaua 240
agaaagccuu ugguaagcuu caaagaagaa cugccaucaa gugaaaaccc cuuuacaagg 300
cuguauaagg aaacuauaga aacauuugac aauaaugaag aagaaucaag cuacucauau 360
gaugagauaa augaucaaac aaaugauaau auaacagcaa gacuagauag gauagaugaa 420
aaauuaagcg agauaauagg aaugcuccau acauuaguug uggcuagugc aggaccaaca 480
gcugcucgug acgguauaag agaugccaug guagggcucc gagaagagau gauugagaaa 540
auaagaucag aagcuuuaau gaccaacgau agguuagaag caauggccag gcuuagggau 600
gaagaaagug aaaagaugac aaaagauaca ucagaugaag uaaaauuaac cccuaccuca 660
gagaagcuga acaugguauu agaagaugaa aguagugaca augaucuauc acuugaagau 720
uucuga 726

<210> SEQ ID NO 16
<211> LENGTH: 241
<212> TYPE: PRT
<213> ORGANISM: Bovine respiratory syncytial virus -continued

<400> SEQUENCE: 16

```
Met Glu Lys Phe Ala Pro Glu Phe His Gly Glu Asp Ala Asn Thr Lys
  1               5                  10                  15

Ala Thr Lys Phe Leu Glu Ser Leu Lys Gly Lys Phe Thr Ser Ser Lys
             20                  25                  30

Asp Ser Arg Lys Lys Asp Ser Ile Ile Ser Val Asn Ser Val Asp Ile
         35                  40                  45

Glu Leu Pro Lys Glu Ser Pro Ile Thr Ser Thr Asn Gln Asn Ile Asn
     50                  55                  60

Gln Pro Ser Glu Ile Asn Asp Thr Ile Ala Thr Asn Gln Val His Ile
 65                  70                  75                  80

Arg Lys Pro Leu Val Ser Phe Lys Glu Glu Leu Pro Ser Ser Glu Asn
                 85                  90                  95

Pro Phe Thr Arg Leu Tyr Lys Glu Thr Ile Glu Thr Phe Asp Asn Asn
            100                 105                 110

Glu Glu Glu Ser Ser Tyr Ser Tyr Asp Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Ile Gly Met Leu His Thr Leu Val Val Ala Ser Ala Gly Pro Thr
145                 150                 155                 160

Ala Ala Arg Asp Gly Ile Arg Asp Ala Met Val Gly Leu Arg Glu Glu
                165                 170                 175

Met Ile Glu Lys Ile Arg Ser Glu Ala Leu Met Thr Asn Asp Arg Leu
            180                 185                 190

Glu Ala Met Ala Arg Leu Arg Asp Glu Glu Ser Glu Lys Met Thr Lys
        195                 200                 205

Asp Thr Ser Asp Glu Val Lys Leu Thr Pro Thr Ser Glu Lys Leu Asn
    210                 215                 220

Met Val Leu Glu Asp Glu Ser Ser Asp Asn Asp Leu Ser Leu Glu Asp
225                 230                 235                 240

Phe
```

<210> SEQ ID NO 17
<211> LENGTH: 60
<212> TYPE: RNA
<213> ORGANISM: Bovine respiratory syncytial virus

<400> SEQUENCE: 17

```
auaucaguua auuccguaga cauagaauua ccuaaagaga guccuauaac aucuaccaau      60
```

<210> SEQ ID NO 18
<211> LENGTH: 20
<212> TYPE: PRT
<213> ORGANISM: Bovine respiratory syncytial virus

<400> SEQUENCE: 18

```
Ile Ser Val Asn Ser Val Asp Ile Glu Leu Pro Lys Glu Ser Pro Ile
  1               5                  10                  15

Thr Ser Thr Asn
             20
```

PRODUCTION OF NOVEL BOVINE RESPIRATORY SYNCYTIAL VIRUSES FROM CDNAS

This application is a continuation-in-part of application Ser. No. 09/554,131, filed Sep. 11, 2000 now abandoned, which is a 371 of PCT/US98/23231, filed Nov. 9, 1998, which claims the benefit of provisional application Ser. No. 60/064,091, filed Nov. 10, 1997. The disclosures of the prior applications are hereby incorporated by reference in their entirety.

INTRODUCTION

Bovine respiratory syncytial virus (BRSV) is a major cause of respiratory tract disease in calves. Respiratory disease is the single most important disease problem of the cattle industry. Seroepizootiologic studies have demonstrated that exposure of cattle to BRSV can vary from mild upper respiratory tract infection to a severe and sometimes fatal interstitial pneumonia.

The genome of BRSV is a single strand of nonsegmented negative-sense RNA of approximately 15,000 nucleotides. Intracellularly, the genomic RNA is transcribed into 10 mRNAs, which encode at least 10 proteins. Of the 10 virus proteins, 8 are structural and 2 are non-structural. Three proteins are contained in the nucleocapsid; specifically the major nucleocapsid protein (N) the phosphoprotein (P), and the large polymerase subunit (L). Three proteins are integral membrane proteins which form the external envelope spikes, namely the attachment glycoprotein (G), the fusion protein (F) and the small hydrophobic protein (SH) of unknown function. There are 2 additional internal virion proteins, namely the matrix (M) protein and a 22 kilodalton protein (M2(ORF1)). The genomic RNA is tightly bound by the major nucleocapsid protein (N) and also is associated with the phosphoprotein (P) and the large polymerase subunit (L). This RNA-protein complex comprises the functional nucleocapsid, which is active in template-dependent RNA synthesis and is packaged in the virion. The M2(ORF1) protein is associated with the nucleocapsid. The functions of the two remaining non-structural proteins (NS1 and NS2) are not clear.

BRSV follows the general scheme of transcription and replication of other nonsegmented negative-strand RNA viruses. The polymerase enters the genome at a promoter in the 3' extragenic leader region and proceeds along the entire length by a sequential stop-start mechanism during which the polymerase remains template bound and is guided by short consensus gene-start (GS) and gene-end (GE) signals. This generates a free leader RNA and 10 nonoverlapping subgenomic mRNAs. The abundance of the various mRNAs decreases with increasing gene distance from the promoter. The genes are separated by short intergenic regions which are not copied into the individual mRNAs. The 3' terminus (leader) and the 5' terminus (trailer) of the genomic RNA contain the cis-acting sequences important for replication, transcription, and the packaging of viral RNA (vRNA). RNA replication occurs when the polymerase somehow switches to a readthrough mode in which the transcription signals are ignored. This produces a complete encapsidated positive-sense replicative intermediate that serves as the template for progeny genomes. A schematic of the genetic map of BRSV is shown in FIG. 1.

The nucleotide sequences for all the 10 mRNAs and all the intergenic sequences of BRSV strain A51908 (ATCC accession no. VR-794) are known. Samal et al. *Virology* 180: 453–456 (1991); Samal et al. *J. Gen. Virology* 72: 1715–1720 (1991); Zamora et al. *J. Gen. Virology* 73: 737–741 (1992); Zamora et al. *Virus Research* 24: 115–121 (1992); Mallipeddi et al. *J. Gen. Virology* 73: 2441–2444 (1992); Pastey et al. *J. Gen Virology* 76: 193–197 (1995); Mallipeddi et al. *J. Gen. Virology* 74: 2001–2004 (1993); Yunus et al. *J. Gen. Virology* 79: 2231–2238 (1998), WO 92/07940, each of which is hereby incorporated by reference. The 45-nucleotide leader sequence at the 3' end and the 162-nucleotide trailer sequence at the 5' end are also known. However, even with all of the knowledge regarding the genetic make-up and the viral mechanism of action of BRSV, it has not been possible to produce a cDNA of the virus, or generate a stable seed of the virus for the subsequent production of attenuated BRSV for vaccines.

A major reason why it has not been possible to produce a cDNA of BRSV is due to the fact that BRSV is a nonsegmented negative-stranded virus. Unlike DNA and positive-stranded RNA viruses, genetic manipulation of negative-stranded RNA viruses has been difficult. This is because (i) genetic recombination has not been detected for these viruses and (ii) the naked RNA (i.e., the vRNA) is not infectious. The vRNA is always tightly wrapped by nucleocapsid proteins and is thought to be the minimum unit of infectivity. Therefore, a recombinant cDNA which insures production of infectious virus in a host cell requires that the cDNA encode not only the vRNA, but also the appropriate viral proteins for transcription and replication to start the first round of virus-specific mRNA synthesis in the host cell.

A few years ago, a breakthrough occurred with the development of methods for introducing individual synthetic genome segments by reassortment into influenza virus, a segmented negative-stranded RNA virus. Luytjes et al. *Cell* 59: 1107–1113 (1989); Enami et al. *Proc. Natl. Acad. Sci. USA* 87: 3802–3805 (1990), hereby incorporated by reference. However, this breakthrough did not solve the problem at hand, because nonsegmented negative-stranded RNA viruses posed additional difficulties because these viruses do not undergo reassortment. Therefore, these viruses required manipulation of the genome as a single piece.

To overcome these additional obstacles, two alternative approaches were developed for nonsegmented negative-stranded RNA viruses. In one approach, synthetic "minigenomes" consisting of genomic terminal sequences surrounding a reporter gene were transcribed from cDNA in vitro and transfected into cells infected with wild type helper virus. Collins et al. *Proc. Natl. Acad. Sci. USA* 88: 9663–9667 (1991); Park et al. *Proc. Natl. Acad. Sci. USA* 88: 5537–5541 (1991); Collins et al. *Virology* 195: 252–256 (1993); Dimock et al. *J. Virol.* 67: 2772–2778 (1993); De et al. *Virology* 196: 344–348 (1993), each of which is hereby incorporated by reference.

The second approach involved co-expression of minigenomes and necessary nucleocapsid proteins from transfected plasmids using the transient vaccinia virus/T7 RNA polymerase expression system. Pattnaik et al. *Cell* 69: 1011–1020 (1992); Calain et al. *Virology* 191: 62–71 (1992); Calain et al. *J. Virol.* 67: 4822–4830 (1993); Conzelmann et al. *J. Virol.* 68: 713–719 (1994); Grosfeld et al. *J. Virol.* 69: 5677–5686 (1995), each of which is hereby incorporated by reference. These approaches have made it possible to begin the characterization of cis- and trans-acting factors required for transcription and replication of several nonsegmented negative-stranded RNA viruses.

However, the prior difficulties were not totally overcome by the new methods, since each synthetic vRNA used represented only a fraction of the parental full-length vRNA. The next challenging step was to determine whether these techniques could be used to rescue full-length vRNA analogs. Recently, the second approach was used to recover complete infectious recombinant virus from full length cDNA for several nonsegmented negative-strand RNA viruses, namely, rabies virus (Schnell et al. *EMBO J.* 13: 4195–4203 (1994)), vesicular stomatitis virus (Lawson et al. *Proc. Natl. Acad. Sci. USA* 92: 4477–4481 (1995); Whelan et al. *Proc. Natl. Acad. Sci. USA* 92: 8388–8392 (1995)), human respiratory syncytial virus (HRSV) (Collins et al. *Proc. Natl. Acad. Sci. USA* 92: 11563–11567 (1995)), measles virus (Radecke et al. *EMBO J.* 14: 5773–5784 (1995)), Sendai virus (Garcin et al. *EMBO J.* 14: 6087–6094 (1995)), and rinderpest virus (Baron et al. *J. Virol.* 71: 1265–1271 (1997)), each of which is hereby incorporated by reference.

Production of infectious BRSV from cloned cDNA would be useful to provide a stable vaccine seed. Presently, there is no satisfactory live attenuated or inactivated vaccine available for prevention of BRSV infection. Subunit vaccines have also not been effective against BRSV infections. Live attenuated vaccines are inexpensive and have been effective against many viral infections. However, at the present time, live attenuated BRSV vaccines are made empirically, and the molecular basis of attenuation is not presently known.

Empirically made live attenuated vaccines are currently made via point mutations on isolated virus particles. Vaccines manufactured according to current procedures may be ineffective or even dangerous since the point mutations can revert back after passage in animals, resulting in active virus. Furthermore, since the starting material is different in each case, it is difficult to achieve desirable levels of attenuation; some viruses are over-attenuated and others are under-attenuated. To make matters more complicated, since there is a high frequency of mutation in RNA viruses, the presently-available attenuated BRSV vaccine stocks are not stable.

An object of the present invention is to produce a cDNA of BRSV which, when inserted into a host cell, is used to produce a stable supply of infectious BRSV. The harvested virus may be used for introducing empirical or, more preferably, site-specific point mutations into the virus to produce more consistent attenuated BRSV vaccines.

Another object of the present invention is to produce an attenuated BRSV having increased or decreased transcription and/or replication, as compared to a wild-type BRSV, through site-specific point mutations introduced on the BRSV.

Recently, Khattar et al. generated a number of deletion and substitution mutations on the N protein of BRSV (*Virology* 270: 215–228 (2000)). The mutations either did not materially affect N protein transcription or replication (between 50–100% of protein transcripts obtained, as compared to wild-type N protein), moderately reduced N protein transcription or replication (between 20–50% of protein transcripts obtained), drastically reduced N protein transcription or replication (between 2–20% of protein transcripts obtained), or completely inhibited N protein transcription or replication (less than 2% of protein transcripts obtained). There is no disclosure or suggestion in Khattar et al. as to producing an attenuated BRSV having increased or decreased transcription and/or replication, as compared to the wild-type.

SUMMARY OF THE INVENTION

The present invention is directed to a synthetic cDNA which codes for an infectious BRSV. The cDNA may be derived from a single strain of BRSV, or it may be a chimeric cDNA which is derived from more than one strain of BRSV. This aspect of the invention also includes vectors and host cells containing the cDNA.

The invention also includes a method of producing infectious BRSV, comprising inserting a synthetic cDNA which codes for an infectious BRSV into a host cell, and expressing the cDNA in the host cell to produce the infectious BRSV. Optionally, the infectious BRSV may thereafter be purified or isolated. This aspect of the invention also includes an infectious BRSV produced by the method.

The invention further includes a vaccine, comprising an infectious BRSV which has been attenuated by introducing at least one empirical or, more preferably, site-specific RNA point mutation thereon, in combination with a pharmaceutically acceptable carrier.

Also included is a method of producing an attenuated BRSV, the method comprising inserting a synthetic cDNA which codes for an infectious BRSV into a host cell, expressing the cDNA in the host cell to produce the infectious BRSV, and thereafter introducing at least one RNA point mutation into the infectious BRSV to attenuate the BRSV.

The invention also includes a method of producing an attenuated BRSV having increased or decreased transcription and/or replication, as compared to a wild-type BRSV. The method comprises inserting a synthetic cDNA which codes for an infectious BRSV comprising a phosphoprotein (P) gene, into a host cell, wherein the cDNA is operably-linked to a promoter, expressing the cDNA in the host cell to produce the infectious BRSV, and thereafter introducing at least one site-specific RNA point mutation on the P gene to produce an attenuated BRSV having increased or decreased transcription and/or replication, as compared to a wild-type BRSV. An attenuated BRSV and vaccine produced by the method are also included.

Between gene-end and gene-start, there are intergenic sequences. The gene-start of the L gene is located 68 nucleotides upstream of the M2 gene-end.

Figure 1:
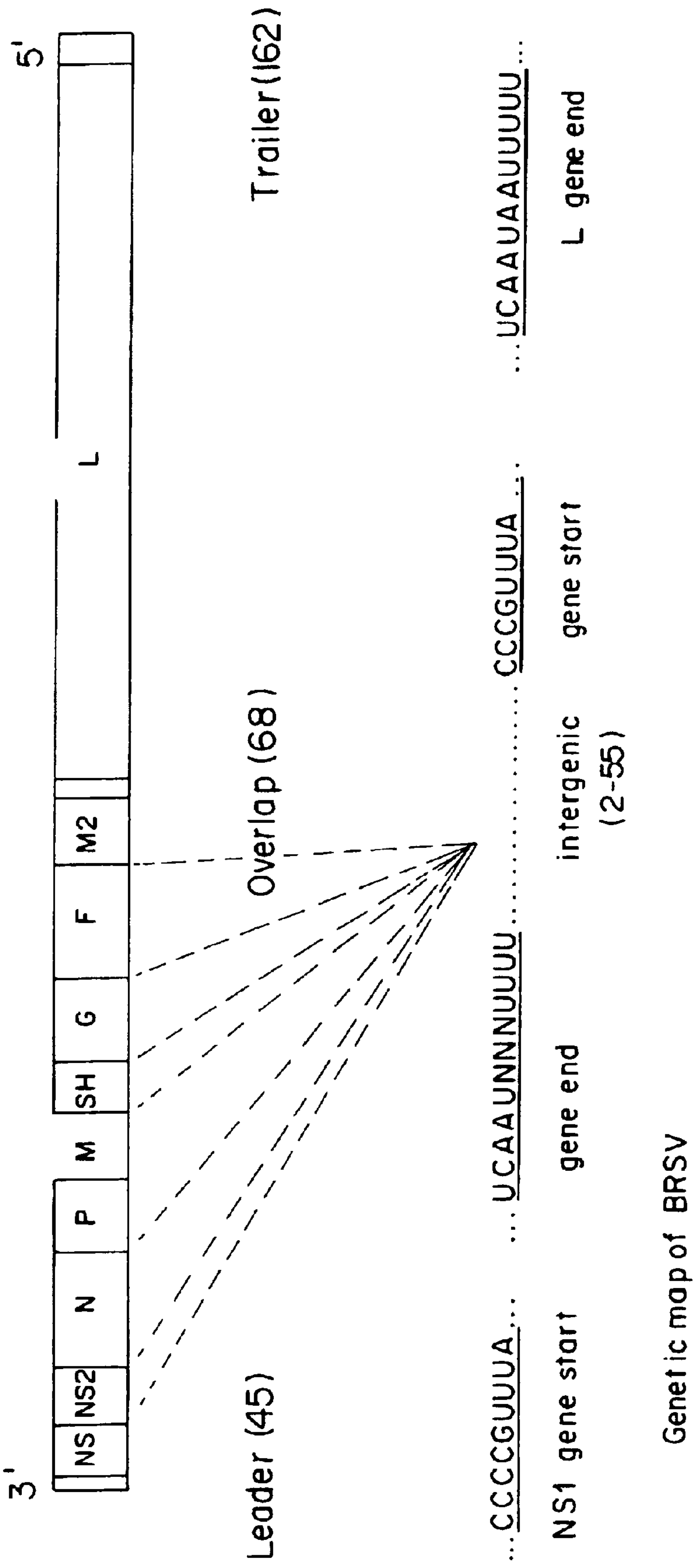
FIG. 1 is a genetic map of BRSV. Genes are identified according to encoded protein (listed within the boxes). Each gene begins with a 9-nucleotide gene-start signal and terminates with a 12- to 13-nucleotide gene-end signal (SEQ ID NO: 1).
Figure 2:
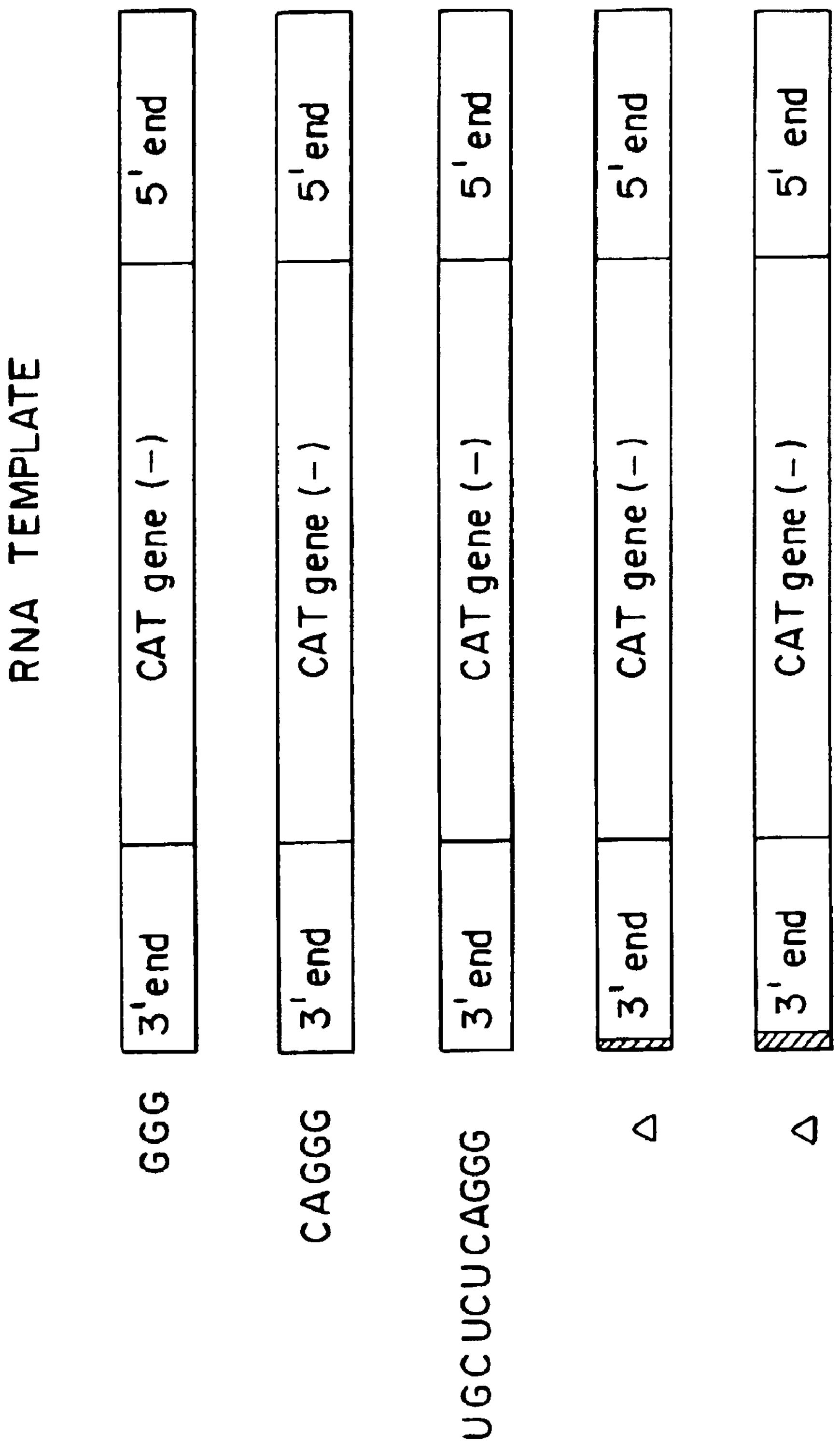

FIG. 2 is a diagram showing additions and deletions of nucleotides at the 3' end of BRSV vRNA analogs (SEQ ID NO: 2).

Figure 3:
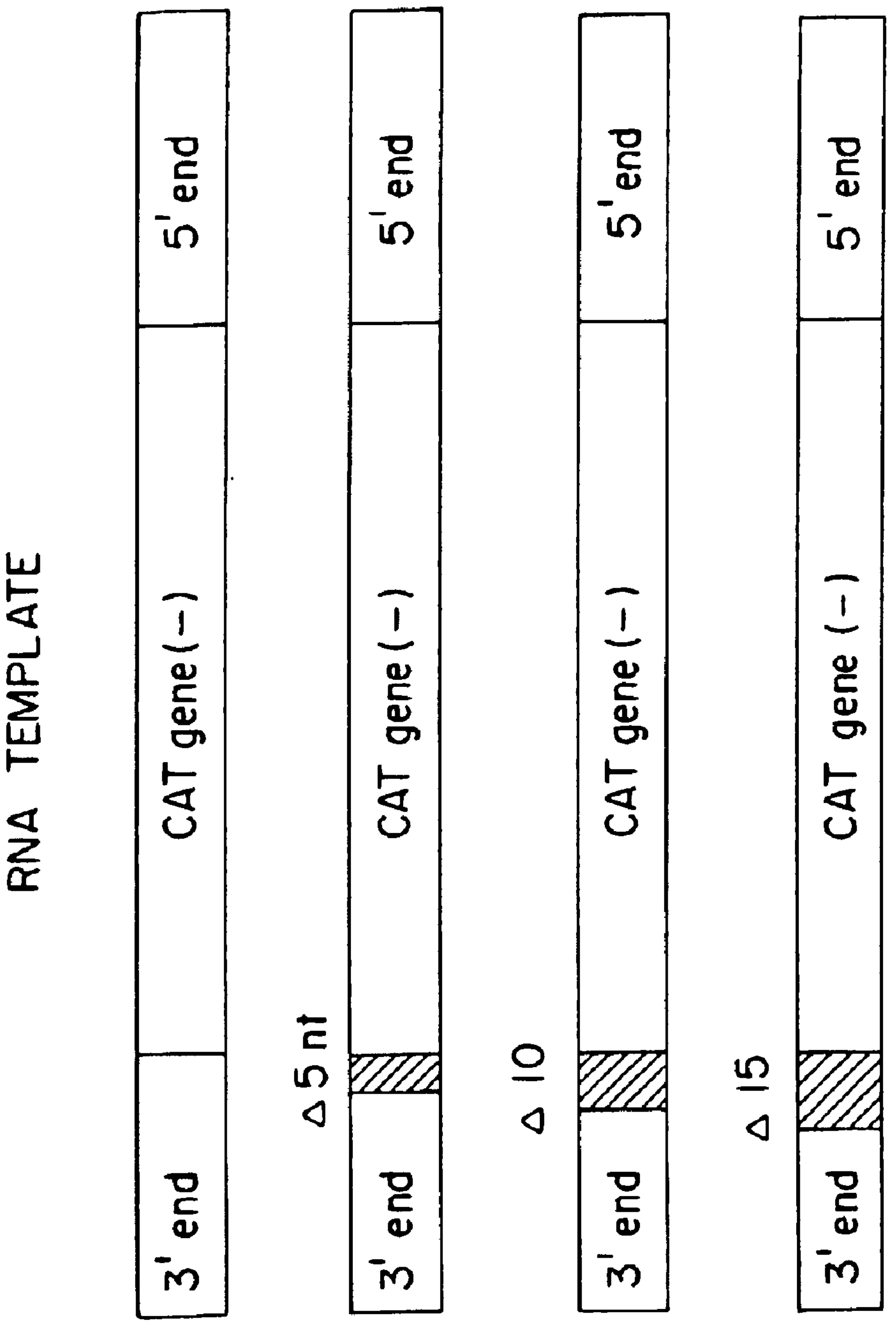

FIG. 3 is a diagram showing deletions of 5, 10 and 15 nucleotides in the leader region.

Figure 4:
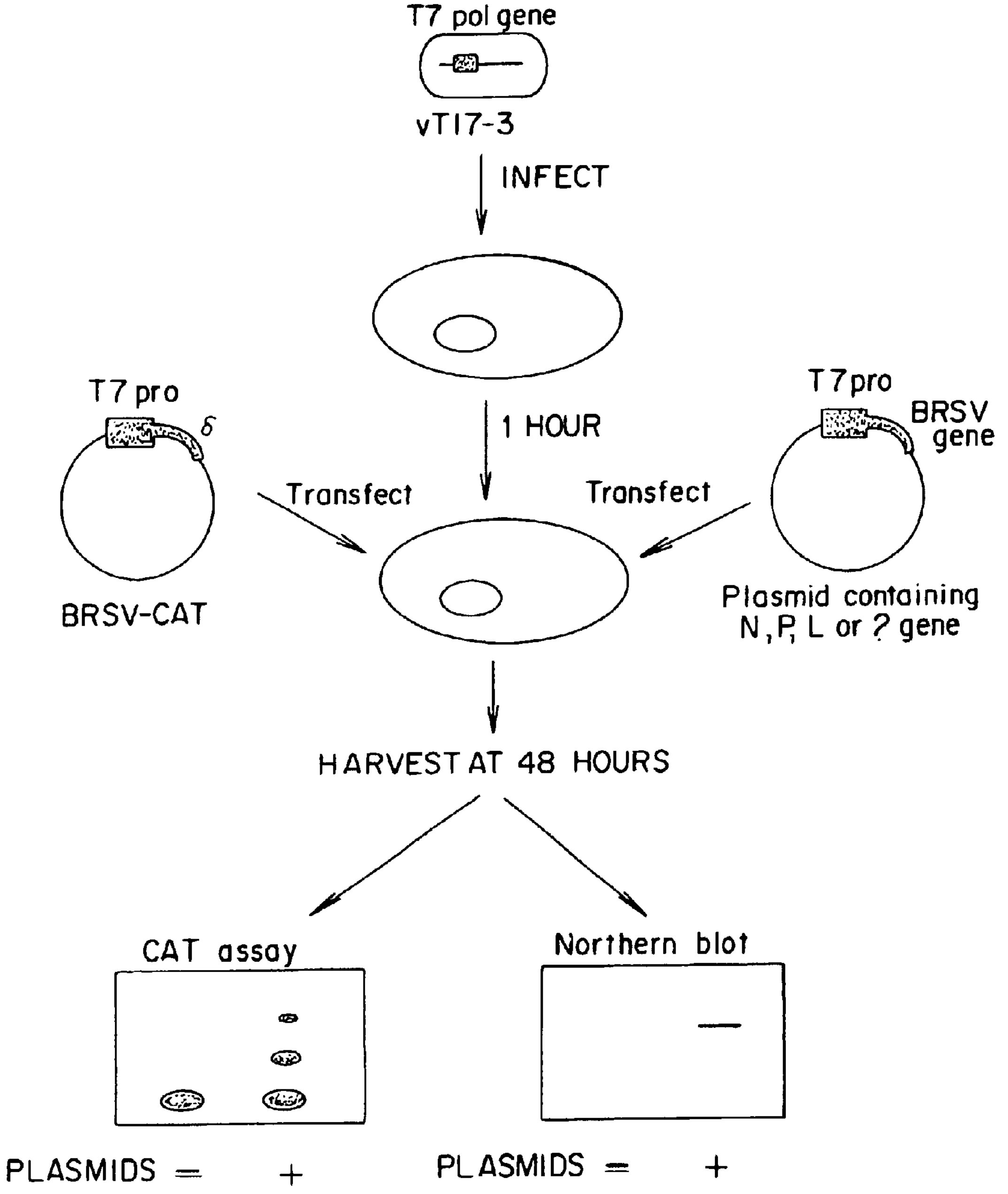

FIG. 4 is a schematic of infection and transfection with plasmid DNAs.

FIG. 5 is a comparison of the leader (SEQ ID NO: 4)and trailer (SEQ ID NO; 6) regions of BRSV with that of HRSV. The leader (SEQ ID NO: 3)and trailer (SEQ ID NO: 5) sequences of HRSV are from Mink et al. *Virology* 185: 615–624 (1991).

Figure 6:
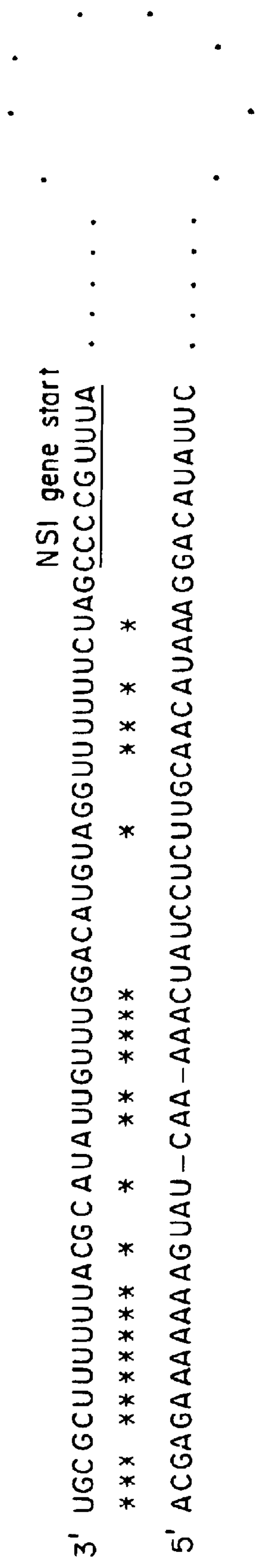

FIG. 6 shows the complementarity between the 3' and 5' ends of BRSV genomic RNA (SEQ ID NOS: 7 & 8).

Figures 7A, 7B, 7C:
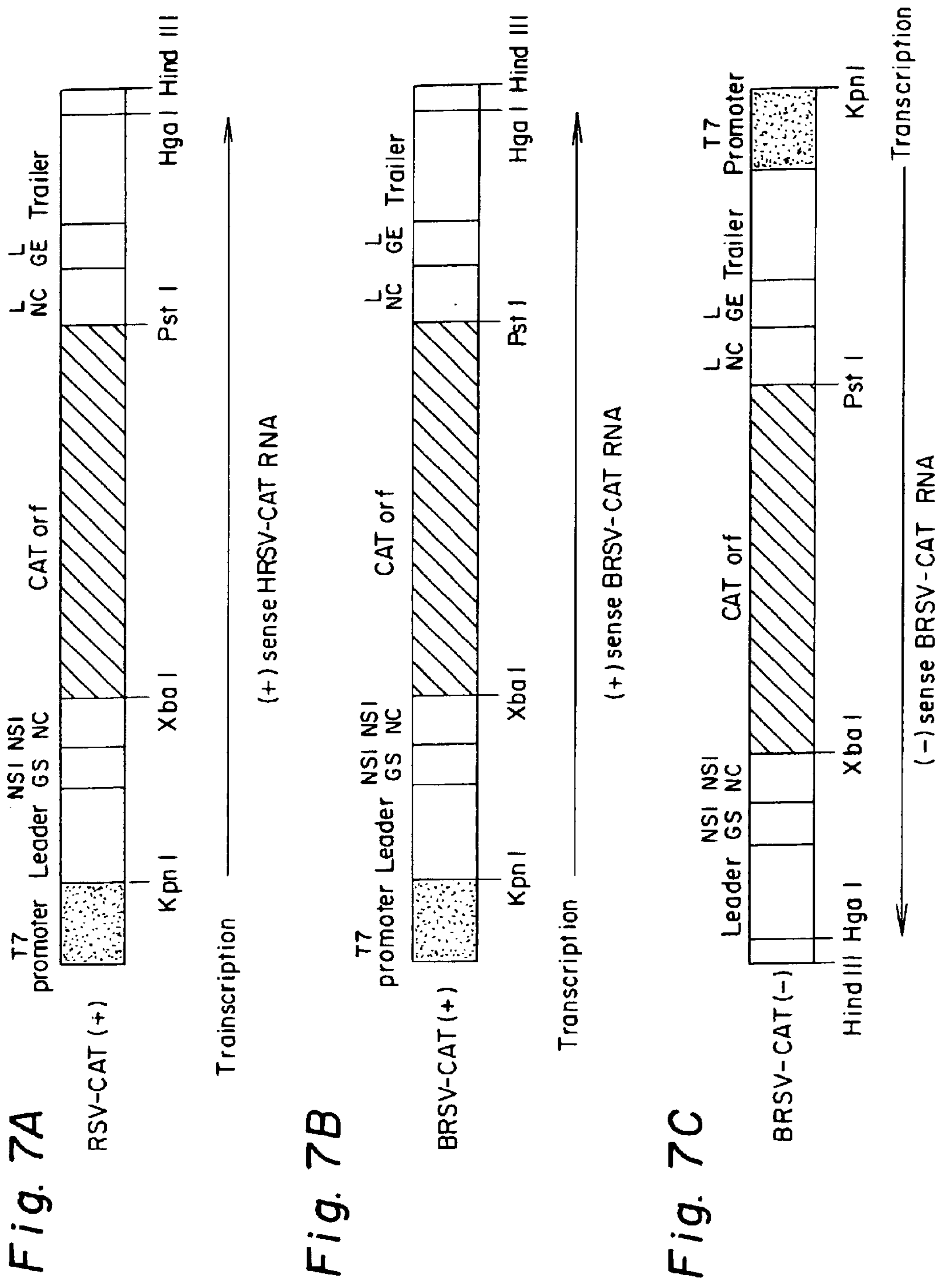

FIG. 7 shows the structures of RSV VRNA analogs containing a CAT marker gene. FIG. 7A shows the structure of HRSV-CAT(+) cDNA; FIG. 7B shows the structure of BRSV-CAT(+) cDNA; FIG. 7C shows the structure of BRSV-CAT(−) cDNA.

Figure 8:
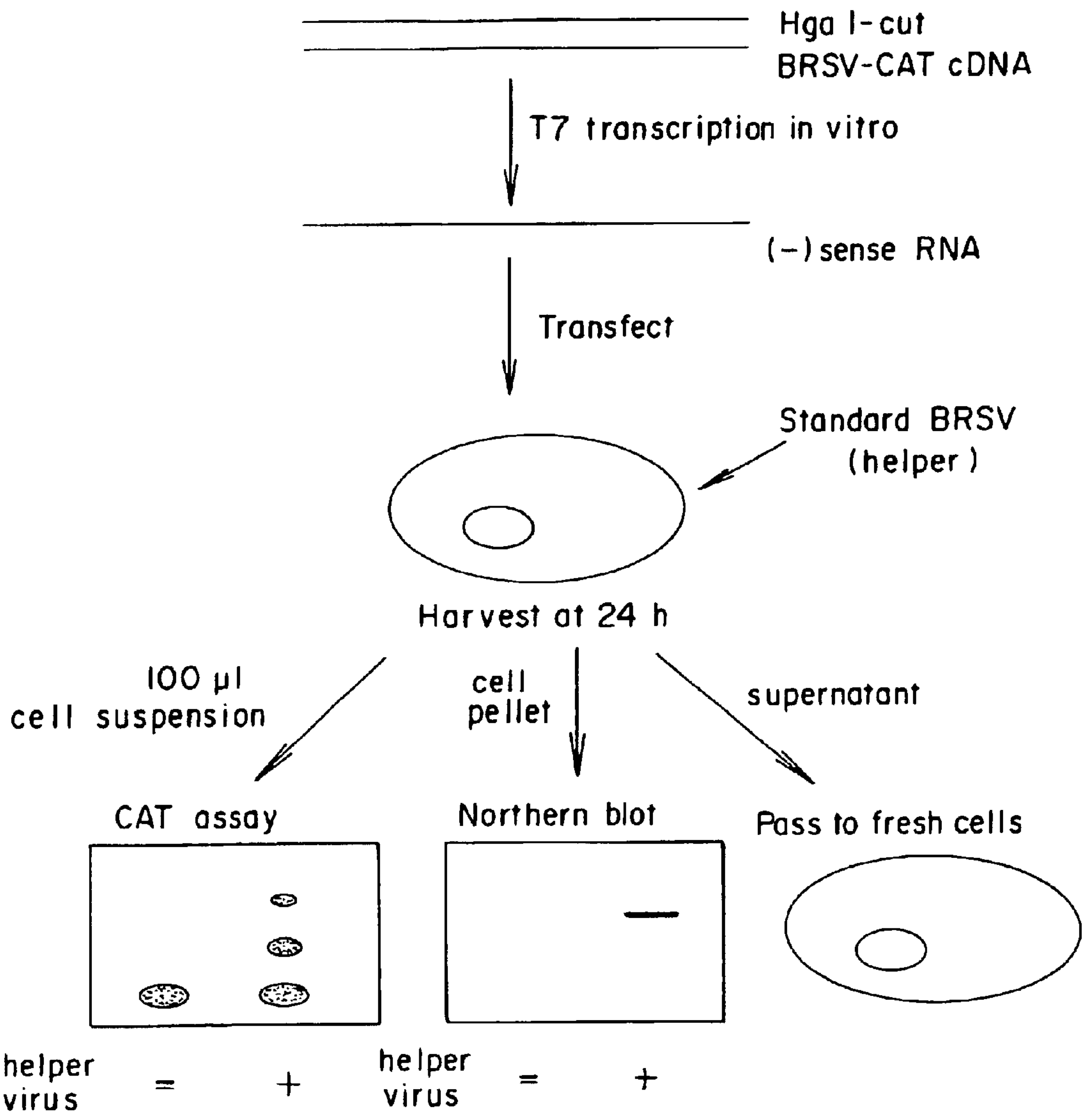

FIG. 8 is a schematic of the RNA transfection and passage experiments disclosed in the present application.

Figure 9:
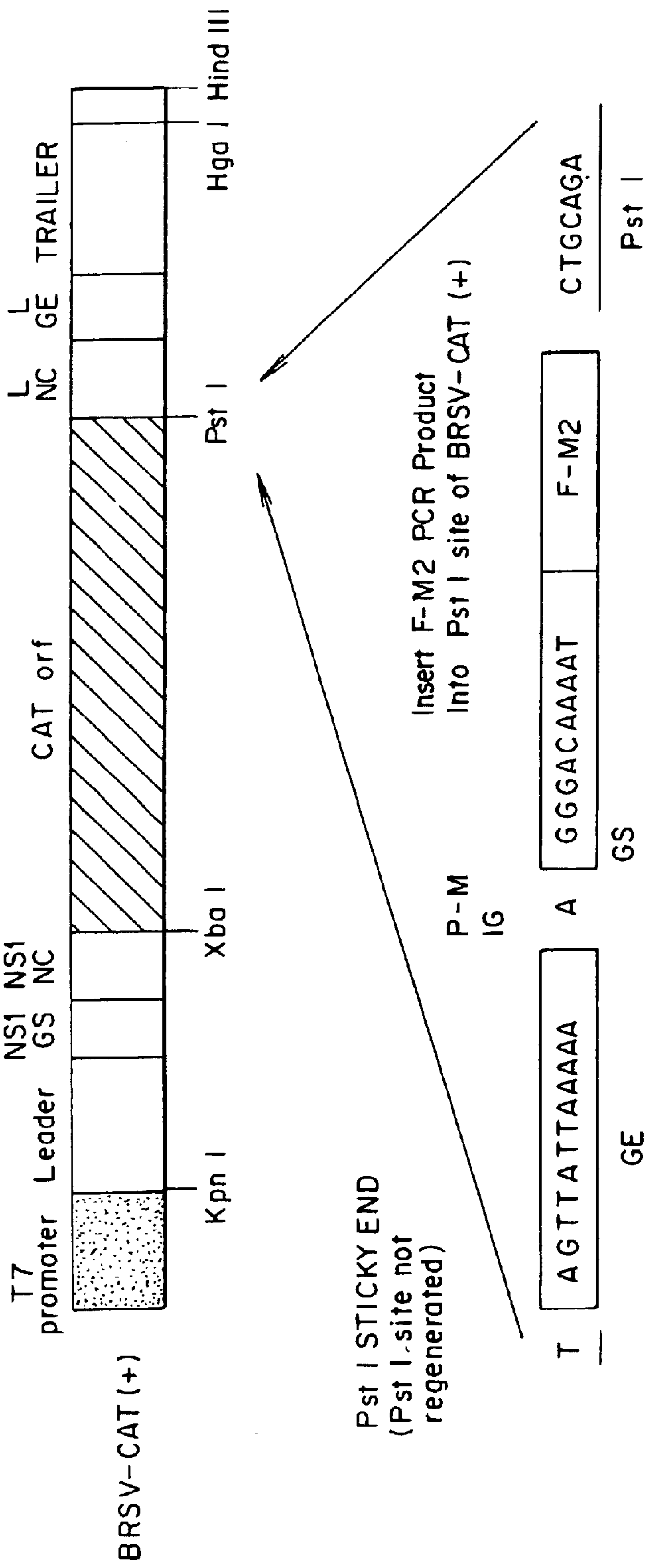

FIG. 9 shows the construction of cDNA (SEQ ID NOS: 9 & 10)encoding BRSV-CAT-F-M2, an analog of BRSV (+)sense RNA containing the CAT, F and M2 genes.

Figure 10:
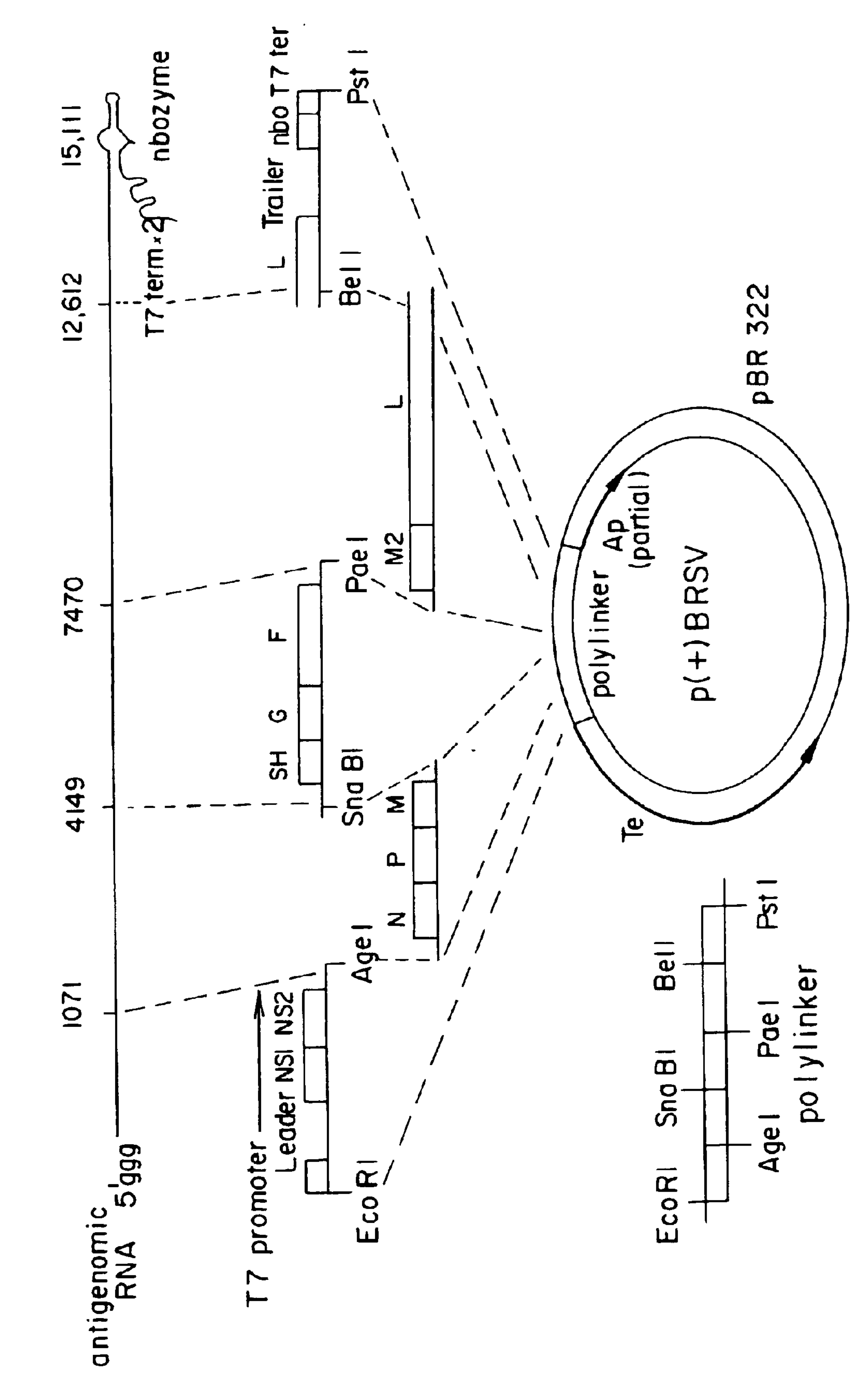

FIG. 10 shows the construction of BRSV antigenomic cDNA and the structure of the encoded proteins.

Figure 11:
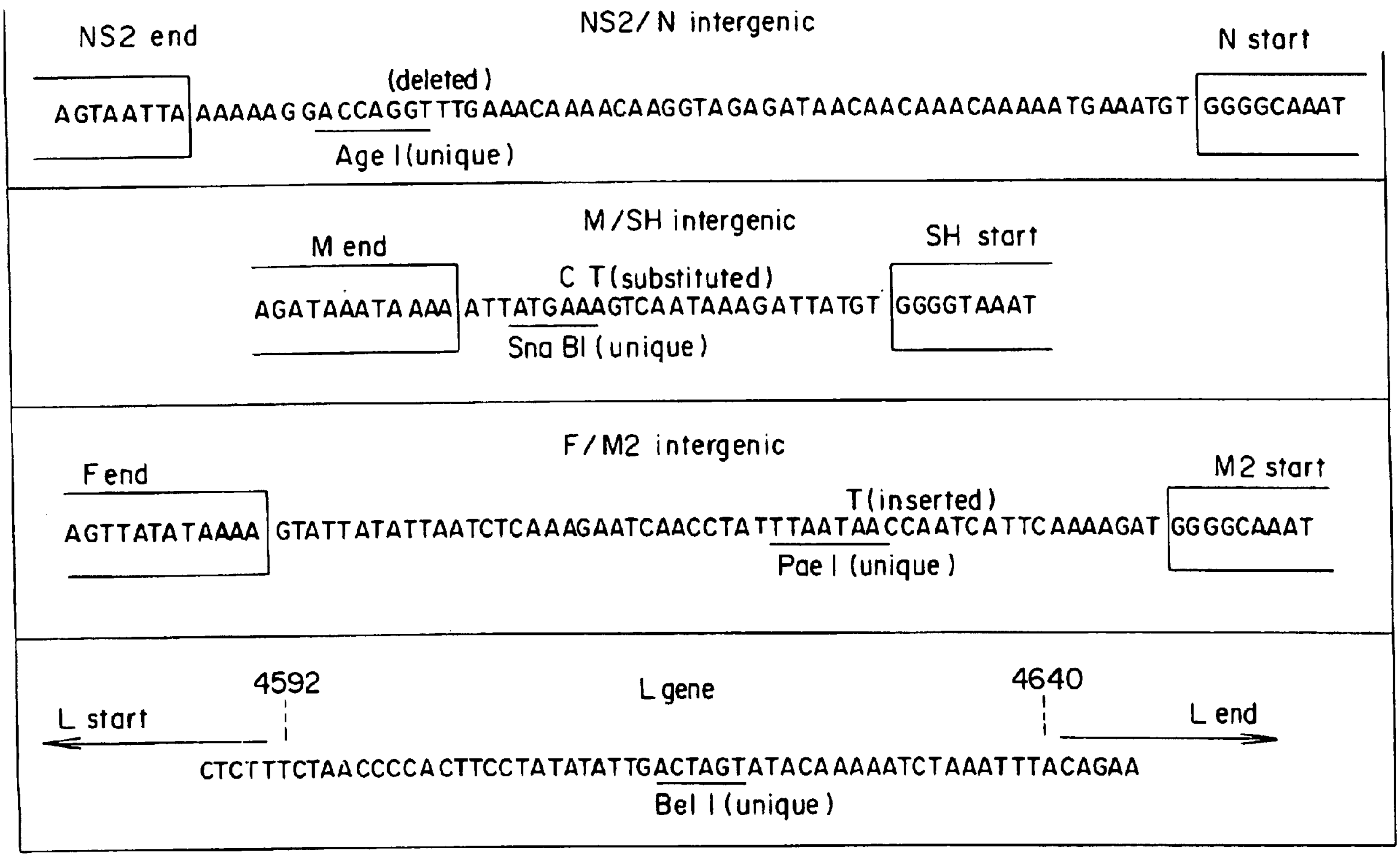

FIG. 11 shows the cDNA markers (SEQ ID NOS 11–14)in the cDNA-encoded antigenomic RNA.

Figure 12:
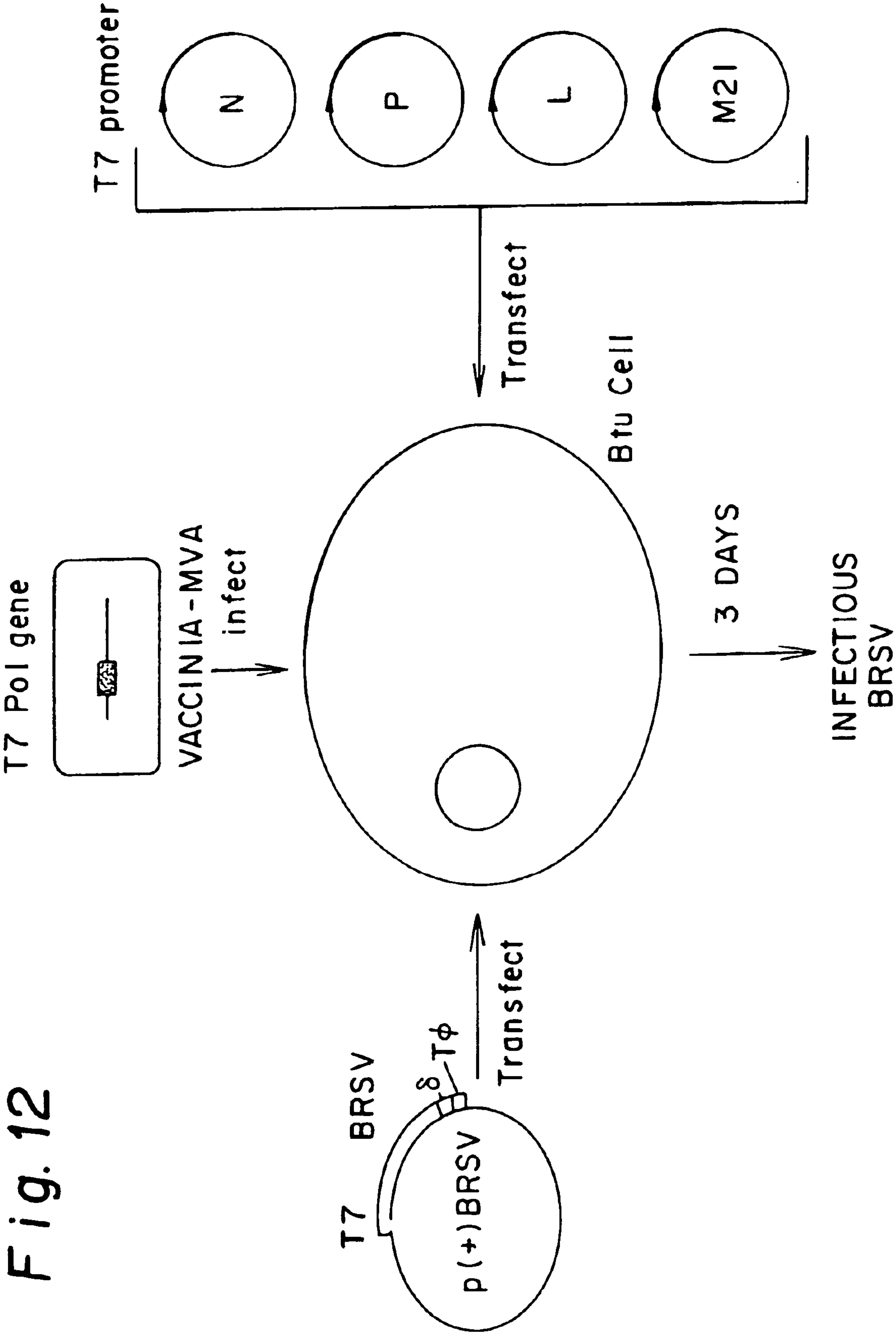

FIG. 12 is a schematic of the transfection and recovery system for rescuing infectious BRSV from cDNA.

DETAILED DESCRIPTION OF THE INVENTION

The term "synthetic cDNA" as used herein means that the cDNA is produced by recombinant DNA technology using scientific techniques known in the art. Preferably, the synthetic cDNA in accordance with the invention is produced by independently preparing several cDNA segments of the BRSV genome, and thereafter ligating the BRSV cDNA fragments to form the functional BRSV cDNA which codes for infectious BRSV.

The cDNA may be derived from a single strain of BRSV, or the cDNA may be a chimeric cDNA which is derived from more than one strain of BRSV. Preferably, the cDNA is from one strain, and more preferably the strain is BRSV strain A51908. However, it is well within the scope of the invention to produce a cDNA containing several ligated cDNA fragments from several different BRSV strains.

The cDNA may be inserted into a vector, such as a plasmid. Preferably, pBR 322 is used as the plasmid vector because large size inserts are more stable in this plasmid. The cDNA can also be inserted into a host cell. DH10B cells (Life Technologies) are preferred in this regard because these cells cause minimal rearrangement of large size plasmids.

Another subject of the invention is a method for producing infectious BRSV. In this method, a synthetic cDNA in accordance with the invention is inserted into a host cell in such a way that the cDNA may be expressed by the host cell (i.e., the cDNA is operably-linked to a promoter), and the cDNA is thereafter expressed in the host cell, whereupon infectious BRSV is produced. The term "operably-linked" broadly includes promoters which are already present in the host cell, or promoters which are physically linked to or inserted independently (at the same or different times) with the cDNA. Useful promoters in this regard are well known to those of skill in the art (Sambrook et al. *Molecular Cloning, A Laboratory Manual*, CSH Laboratory Press (1989); Ausubel et al. *Current Protocols in Molecular Biology*, Greene Publishing and Wiley Interscience, New York (1991), each of which are hereby incorporated by reference). The promoter for T7 RNA polymerase is preferred. The host cell in this regard is preferably a bovine turbinate (Btu) cell. The infectious BRSV produced in accordance with the method may thereafter be purified or isolated from the host cell and/or the culture medium. Also included within the scope of the present invention is infectious BRSV produced in accordance with the method of the invention described above.

The present invention also includes a method of producing an attenuated BRSV having increased or decreased transcription and/or replication, as compared to a wild-type BRSV. The method comprises inserting a synthetic cDNA which codes for an infectious BRSV comprising a phosphoprotein (P) gene, into a host cell, wherein the cDNA is operably-linked to a promoter, expressing the cDNA in the host cell to produce the infectious BRSV, and thereafter introducing at least one site-specific RNA point mutation on the P gene to produce an attenuated BRSV having increased or decreased transcription and/or replication, as compared to a wild-type BRSV. An attenuated BRSV and vaccine produced by the method are also included.

The sequence of the wild-type P gene (SEQ ID NO: 15)and protein (SEQ ID NO: 16)is disclosed, for example, in SEQ ID NO: 6 of WO 92/07940, and the protein is also disclosed in GenBank Accession No. P33454, each of which is hereby incorporated by reference. The numbering of the gene bases, sequences, codons or amino acids referred to throughout the specification and claims is measured on the wild-type P gene and protein as disclosed in these references.

The introduction of at least one site-specific RNA point mutation in the majority of loci of the P gene of BRSV produces an attenuated BRSV having decreased transcription and/or replication, as compared to a wild-type BRSV. However, it has surprisingly been found that the introduction of at least one site-specific RNA point mutation in certain regions of the P gene produces an attenuated BRSV having increased transcription and/or replication, as compared to a wild-type BRSV. This was unexpected since prior studies had determined that all site-specific mutations on the N gene decreased transcription and/or replication, as compared to the wild-type.

Preferably, in order to increase the transcription and/or replication of the BRSV, the point mutation(s) on the P gene are made between codons 41–60 (SEQ ID NO: 17) of the P gene (corresponding to amino acids 41–60 of the P protein), as measured on the wild-type P gene. It is preferred that at least two, more preferred that at least three, and most preferred that at least four point mutations are made on the P gene (for increased transcription and/or replication, between codons 41–60 of the P gene). It is preferred that the point mutations are deletions, however substitutions are also possible. In a preferred embodiment, at least five codons, more preferably at least eight or at least twelve, are deleted. In the most preferred embodiment for increasing transcription and/or replication, codons 41–60 of the P gene are deleted.

Without being bound by theory, a region of codons between 41–60 of the P gene appears to be responsible for negative regulation of transcription and/or replication. In order to increase transcription and/or replication of BRSV, this region of codons is preferably deleted, modified or otherwise rendered unreadable, using tools (such as antisense) available to those of ordinary skill in the art.

Subject matter of the present invention is also a vaccine comprising an infectious BRSV produced in accordance with the invention which has been attenuated by introducing at least one RNA point mutation thereon. Empirical point mutations on virus particles may be made by chemical treatment, heating, drying, irradiation, or any other method in accordance with knowledge of the art. It is especially preferred that the point mutation is site-specific (at a predetermined gene locus), carried out in accordance with the state of the art. See, for example, Byrappa et al., *Genome Res*. 5: 404–407 (1995), hereby incorporated by reference.

The term "point mutation" as used herein means a nucleic acid substitution and/or deletion. Preferably when increased transcription and/or replication is desired, the point mutation (s) on the P gene produce an attenuated BRSV which has at least 1.5 times, preferably at least two times, increased transcription and/or replication, as compared to a wild-type BRSV. When decreased transcription and/or replication is desired, the point mutation(s) on the P gene produce an attenuated BRSV which has little reduction on transcription and/or replication (between 50–99% of protein transcripts obtained, as compared to wild-type protein), moderately reduced transcription and/or replication (between 20–50% of protein transcripts obtained), drastically reduced transcription and/or replication (between 2–20% of protein transcripts obtained), or completely inhibited protein transcription and/or replication (less than 2% of protein transcripts obtained).

The invention will be further described by the following Examples.

EXAMPLE 1

Construction and Rescue of BRSV Minigenomes

A cDNA was constructed to encode a 953-nucleotide, internally deleted version of BRSV genomic RNA, (BLT (−)), in which the viral genes were replaced with the bacterial chloramphenicol acetyl transferase (CAT) reporter gene. The CAT gene was flanked in turn by sequences representing (i) noncoding sequences of the first and last genes in the BRSV genome, (ii) BRSV gene-start and gene-end sequences, and (iii) 3' leader and 5' trailer sequences of BRSV genomic RNA. A second cDNA, BLT (+), is a positive-sense RNA which would correspond to the predicted replicative intermediate of BRSV-CAT genomic RNA. The procedure for constructing the cDNA was as follows.

i. Nucleotide Sequences of 3' Leader and 5' Trailer Regions of BRSV Strain A51908

RNAs with 3 extra Gs, an extra GGGAC, or 11 extra nucleotides and a deletion of 1 or 5 nucleotides at the 3' terminus were tested for promoter activity (FIG. 2). Mutant plasmids were generated by PCR with primers containing these additions and deletions between the T7 promoter sequence and the 3' terminus sequence of BRSV leader region. The presence of these additions or deletions in the plasmids was confirmed by DNA sequencing. Transcription from T7 promoter caused insertion of 3 non-viral G residues at the 3' end of transcripts. This was considered as the wild-type promoter. Therefore, only the addition of an extra 2 and 8 nucleotides between T7 promoter sequence and the 3' end of the leader sequence was necessary. CAT activity and RNA replication of all constructs after transfection and passage was examined. CAT activity below 50% of that of the wild-type promoter was considered significant. RNA replication was analyzed by Northern blot. The RNA bands on the Northern blots were quantitated using a phospho imager. To confirm whether the additions and deletions of nucleotides at the 3' end of the vRNA were retained during replication, the 3' and 5' ends of the RNA template were sequenced following 5'-3' RNA ligation and RT-PCR (see Mandl et al. *Biotechniques* 10: 485–486 (1991)). Briefly, total RNA from one dish of a 6-well plate was purified using Trizol reagent. The total RNA was decapped with tobacco acid pyrophosphatase (Epicentre Technologies). The decapped RNA was circularized by use of RNA ligase (see Romaniuk et al. *Methods Enzymol.* 100: 52–59 (1983)), cDNA synthesis (see Gubler et al. *Gene* 25: 263–269 (1983)) across the ligated termini, and amplification of the junction region by PCR.

The 3' leader region of BRSV is 45 nucleotides, which contains the promoter sequence for transcription and replication. To define the minimum promoter sequences, plasmids were generated with progressively larger internal sequence deletions. In BRSV and other negative-stranded RNA viruses there is terminal complimentarity, which was retained in all deletion constructs. Three plasmids were constructed in which deletions of 5, 10 and 15 internal nucleotides of the leader region were made (FIG. 3). These constructs were generated by PCR. Effects of these deletions on transcription and replication was examined by CAT assay and Northern blot analysis, respectively.

The 5' trailer region contains the promoter sequence necessary for synthesis of negative sense RNA. To define the minimum promoter sequence, plasmids were generated with progressively larger upstream sequence deletions. Initially, 3 plasmids were constructed in which deletions of 50, 75 and 150 internal nucleotides of the trailer region were made. These constructs were generated by PCR. Effects of these deletions on transcription and were examined by CAT assay.

The BRSV proteins necessary for the various steps in the BRSV growth cycle were identified using a recombinant vaccinia virus T7-based expression system (see Fuerst et al. *Mol. Cell. Biol.* 7: 2538–2544 (1987)). cDNA clones of the 10 BRSV genes were placed in T7-based plasmids, and correct expression has been confirmed for all genes.

In this system, the cDNA was transfected into cells. T7 polymerase was supplied by infection with a vaccinia-T7 recombinant virus and transcription was performed intracellularly. The cDNA was modified to contain a self-cleaving ribozyme motif. Accordingly, the BRSV-CAT constructs were modified to contain a hepatitis delta virus (HDV) genomic ribozyme sequence (see Perrotta et al. *Nucl. Acids Res.* 18: 6821–6827 (1990); Perrotta et al. *Nature* (*London*) 350: 434–436 (1991)) in place of the Hga I site to execute self-cleavage. Addition of the ribozyme sequence was done by 3 successive PCRs. In the first round of PCR, the forward primer contained Hind III and T7 promoter sequences and the reverse primer contained 20 nucleotides of the leader plus 40 nucleotides on the 3' side of the ribozyme cleavage site. In the second and third rounds of PCR, the same forward primer and new reverse primers were used to add the rest of the ribozyme sequence followed by T7 terminator sequence and a Kpn I site. The final PCR product was digested with Hind III and Kpn I and cloned into the Kpn I-Hind III window of pUC 19. The entire sequence was confirmed by DNA sequencing.

It was confirmed that the N, P and L proteins are sufficient for RNA replication. Briefly, Mandin-Darby bovine kidney (MDBK) cells were infected with the recombinant vaccinia virus vTF7-3 (multiplicity of infection of 10) which expresses the T7-RNA polymerase (obtained from ATCC, Herndon, Va.). One hour after infection, cells were transfected using LipofectACE, with BRSV-CAT(−) plasmid and various combinations and relative molar amounts of T7-based plasmids containing N, P and L genes. Cells and supernatants were harvested 48 hours after infection for CAT assays and Northern blot analysis using (−) RNA probe (FIG. 4), which hybridizes only to (+) sense RNA made from BRSV-CAT(−) RNA. Conversely, to detect the synthesis of (−) RNA from antigenomes, cells were transfected with BRSV-CAT(+) plasmid and probed with (+) sense probe.

To determine the role of each BRSV protein in transcription and replication, all BRSV proteins were coexpressed in various combinations and relative molar amounts from cDNA using the vaccinia virus/T7 RNA polymerase expression system. Briefly, the cells were infected with vaccinia virus recombinant vTF7-3. One hour after infection, cells were transfected with BRSV-CAT(+) plasmid and various combinations of T7-based plasmids containing BRSV genes. Cells and supernatants were harvested 48 hours after infection for CAT assays and Northern blot analysis.

To determine the BRSV proteins required for formation of virus-like particles, cells were infected with vTF7-3 for 1 hour and cotransfected with BRS-VCAT(+) plasmid and various combinations of T7-based plasmids containing BRSV genes for 3 hours. Then the transfection medium was replaced with growth medium containing 100 $\mu$ci/ml of $^3$H-uridine. Forty-eight hours after infection, cells were harvested by scraping and were pelleted by centrifugation at 8000 times g for 1 minute in a microcentrifuge. 100 $\mu$l of the supernatants were immunoprecipitated with antisera to N, G and F proteins, and with normal rabbit serum. The immunoprecipitates were collected with Staph. prot. A. and counted in a liquid scintillation counter.

Nucleotide Sequences of the 3' Leader and 5' Trailer Regions

The nucleotide sequences of the 3' extragenic leader and 5' extragenic trailer regions were determined for genomic RNA (vRNA) of BRSV strain A51908 (FIG. 5). To sequence the 3' leader region, VRNA was extracted from purified virions and ligated to a synthetic RNA of known sequence. cDNA was made using reverse transcription (RT)-PCR. The 3' leader of BRSV is 45 nucleotides. The 5' trailer region of BRSV VRNA was determined by 5' RACE method. Both G and C trailing reactions were performed to determine the 5' terminal nucleotide. The 5' trailer of BRSV is 162 nucleotides in length. The 3' and 5' ends of BRSV vRNA are partially complementary (FIG. 6), suggesting that similar sequences at the 3' end of the genome and antigenome function similarly during replication.

ii. Construction of BRSV-CAT(+) and BRSV-CAT(−) cDNA

BRSV-CAT(+) cDNA was constructed from RSV-CAT cDNA (available from Dr. P. L. Collins, NIH, Bethesda, Md.). AcDNA clone that contained the NS1 gene and leader region of BRSV and was used to obtain BRSV leader sequences was amplified by PCR. The forward primer contained a Kpn I site, T7 promoter and 3' terminal 20 nucleotides of the leader region. The reverse primer contained an Xba I site and the last 20 nucleotides of the NS1 non-coding region. The amplified product was digested with Kpn I and Xba I and then was used to replace the Kpn I-Xba I fragment of RSV-CAT (FIG. 7A). Similarly, a cDNA clone that contained the downstream portion of the L gene and the trailer region of BRSV was amplified by PCR. The forward primer contained a Pst I site and 20 nucleotides of the L gene non-coding region and the reverse primer contained Hind III and Hga I sites and 5' terminal 20 nucleotides of the trailer region. The amplified product was digested with Hind III and Pst I and was then used to replace the Pst I Hind III fragment of the previous construct. Conventional conditions of PCR, gel purification, ligation and cloning were followed. See Ausubel et al. *Current Protocols in Molecular Biology*, Greene Publishing and Wiley Interscience, New York (1991). The sequence of the BRSV-CAT(+) (FIG. 7B) was confirmed by dideoxynucleotide sequencing.

BRSV-CAT(−) cDNA was constructed from BRSV-CAT (+) by PCR (FIG. 7C). The forward primer contained a Kpn I site, T7 promoter and 5' terminal 20 nucleotides of the trailer region. The reverse primer contained Hind III and Hga I sites and 3' terminal 20 nucleotides of the leader region. The amplified product was digested with Kpn I and Hind III and then cloned into Kpn I-Hind III window of a modified form of pBluescript II KS+ that lacked the T7 promoter. The sequence of BRSV-CAT(−) was confirmed by dideoxynucleotide sequencing.

iii. In vitro Transcription and Transfection

Hga I digested plasmid DNA (2 $\mu$g/100 $\mu$l) was transcribed in vitro with T7 RNA polymerase according to protocols provided by the supplier (Promega). Transcription was for 3 hours at 37° C.

MDBK, bovine turbinate (Btu), and 293 cells were examined for high consistent expression of CAT. All these cell lines support growth of BRSV. A schematic of the RNA transfection and passage experiments are shown in FIG. 8. Briefly, cells maintained in monolayer cultures in 6-well dishes in minimal essential medium (MEM) containing 10% fetal bovine serum (FBS) was infected with 5 to 10 PFU of BRSV per cell in a volume of 1 ml per well and incubated for 1 hour at 37° C. The cells were washed twice with Opti-MEM 1 (Life Technologies) and incubated for 3 hours at 37° C. with a mixture containing 1 ml of Opti-MEM 1, 12 $\mu$l of LipofectACE (Life Technologies) and approximately 2–5 $\mu$g of in vitro-synthesized RNA (2 to 10 $\mu$l of transcription reaction). The transcription mixture was removed, the cells were washed once with growth medium (MEM supplemented with 10% FBS and 2 mM glutamine) and fed with 1.5 ml of growth medium. At 20 to 24 hours after infection, cells were harvested for CAT assays and RNA analysis. Cells were harvested by scraping and a 100 $\mu$l aliquot of cell suspension was kept aside for CAT activity. The remaining cell suspension was pelleted by centrifugation at 8000 times g for 1 minute at 4° C. in a microcentrifuge. The cell pellet was processed for total RNA purification using Trizol reagent (Life Technologies) following manufacturer's instructions with the modification that after isopropanol precipitation, RNAs were purified additionally with phenol+chloroform mixture and precipitated with ethanol. The RNA pellet was dissolved in 50 $\mu$l of water and stored at −80° C. until Northern blot analysis.

A 100 $\mu$l cell suspension kept aside from the transfection experiment was assayed for CAT activity using standard procedures (see Ausubel et al., supra; Gorman et al. *Mol. Cell. Biol.* 2: 1044–1051 (1982)). Briefly, cell lysate was prepared by three cycles of freezing and thawing. Lysates were incubated in the presence of $^{14}$C chloramphenicol and acetylation was monitored by thin layer chromatography and quantitated by liquid scintillation counting of excised spots.

Approximately 15$\mu$g of total RNA purified using Trizol reagent was examined by Northern blot analysis. RNAs were separated by electrophoresis on small (7 cm long×10 cm wide) gels of 1.5% agarose in 0.41 M formaldehyde. Gels were blotted onto nitrocellulose membrane using an alkaline transfer buffer (see Thomas *Proc. Natl. Acad. Sci. USA* 77: 5201–5205 (1980)). RNAs were fixed on the nitrocellulose membrane by UV irradiation (Stratagene), prehybridized for 6 hours at 65° C. in 6×SSC, 0.2 mg/ml sheared denatured salmon sperm DNA, 5×Denhardt's solution, and 0.1% sodium dodecyl sulfate (SDS), and hybridized for 12 hours in the same solution containing approximately 5×10$^6$ cpm $^{32}$P-RNA per blot. Blots were washed (2×15 minutes) at room temperature in 2×SSC-0.1% SDS and (2×15 minutes) at 65° C. in 0.1×SSC-0.1% SDS. Radiolabeled RNA probes were synthesized under conditions of reduced CTP concentration and in the presence of $^{32}$P-CTP as described by the supplier (Promega). The reaction was treated with DNase, extracted with phenol+chloroform and passed through a column of Sephadex G-50 to remove unincorporated label.

iv. Incorporation into Virus-like Particles

To test whether BRSV-CAT VRNA analog was packaged into virions, supernatants from the infected-transfected cells were clarified of cells, and 100 μl of this supernatant was used to infect fresh cells. For antibody inhibition studies, the anti-BRSV serum or anti-bovine P13 virus serum was added to the inoculum prior to infection and incubated for 30 minutes at 37° C. At 24 hours after infection, cells were harvested for CAT assays and Northern blot analysis. Inhibition of CAT activity and RNA replication by anti-BRSV serum but not by antibovine P13 serum showed that the vRNA analogs were packaged into virus-like particles.

EXAMPLE 2

Construction and Rescue of BRSV Midigenomes

BRSV-CAT is only a fraction of the length of the BRSV vRNA. Therefore, "midigenomes" were generated containing several BRSV genes. The F and M2 genes of BRSV were inserted downstream from the CAT, and produced a BRSV-CAT-F-M2 construct of 3860 nucleotides in length.

To construct the midigenome, the dicistronic F-M2 cDNA (clone 162) containing complete F and M2 genes was used (see Zamora et al. *J. Gen. Virology* 73: 737–741 (1992)). This cDNA was modified by PCR to contain a Pst I site, gene-end and intergenic sequences followed by the gene-start of the F gene and a Pst I site after the gene-end sequence of the M2 gene (FIG. 9). To avoid any possible nucleotide misincorporation during PCR amplification, Pfu DNA polymerase (Stratagene) and 15 amplification cycles were used.

The F-M2 PCR product was digested with Pst I and inserted into the Pst I site of the BRSV-CAT(+) construct. The F and M2 genes in the BRSV-CAT-F-M2 construct were sequenced using F and M2 primers. Positive-sense transcripts were used because large amounts of positive-sense N-, P- and L-specific RNAs were produced from the transfected protein-encoding plasmids, which can hybridize negative-stranded genomic RNA transcripts containing these genes.

Transfection experiments were carried out with cells which had been infected 1 hour previously with recombinant vaccinia virus vTF7-3. BRSV-CAT-F-M2 positive-sense transcript and plasmids containing genes for protein required to make active nucleocapsids were used for transfection. After 48 hours, transfected cells were examined for expression of F and M2 genes by immunofluorescence and immunoprecipitation using antibodies to F and M2 proteins. (See Ausubel et al., supra.) Northern blot analysis of total RNA with positive-sense F and M2 RNA probes were used to confirm that transcripts of F and M2 genes were generated intracellularly by the BRSV polymerase protein and the input positive-sense CAT-F-M2 transcript was replicated to negative-sense RNA by the T7 polymerase enzyme expressed from the recombinant vaccinia virus.

EXAMPLE 3

Construction of BRSV cDNA Clone

A cDNA clone encoding the antigenome of BRSV strain A51908 was constructed from cDNA segments which were synthesized by reverse-transcription (RT)-coupled PCR from virion-derived genomic RNA (FIG. 10).

Genomic RNA was extracted from purified BRSV using Trizol reagent according to the manufacturer's instructions (Life Technologies). RT was carried out using superscript RT (Life Technologies) and PCR was carried out using Pfu polymerase (Stratagene). The leader end was constructed to join the promoter for T7 RNA polymerase which included three transcribed G residues for optimal activity. Transcriptions generated three non-viral G residues at the 5' end. To generate a nearly exact 3' end, the trailer end was constructed to join the HDV antigenome ribozyme sequence followed by tandem terminators of T7 transcription (see Perrotta et al. (1991) supra).

It has been shown that the noncoding intergenic sequences of RSV are not critical for transcription and replication of vRNA (Kuo et al. *J. Virol.* 70: 6143–6150 (1996)). Therefore, these intergenic regions can be used to assemble functional BRSV cDNA. Four unique restriction site markers (FIG. 11) were introduced into the intergenic region of the antigenomic DNA by incorporating the changes into the oligonucleotide primers used in RT-PCR. RT-PCR fragments were cloned into a modified version of pBR 322 in which the Pst I-EcoRI fragment was replaced with a synthetic polylinker containing unique restriction sites designed to facilitate assembly. Initially, each cDNA fragment was cloned separately and the correct sequence was confirmed by DNA sequencing. Then all the BRSV cDNA fragments were ligated to form the functional BRSV cDNA.

The antigenomic cDNA was completely sequenced to determine the correct sequence. The sequence data showed misincorporation of two nonviral nucleotides, one in the open reading frame of the NS1 gene and the other in the open reading frame of the M2 gene. To correct these misincorporations, cDNA segments carrying these 2 genes were amplified by RT-PCR. Three independent RT-PCRs for each gene were carried out using only 18 cycles of PCR. These segments were completely sequenced. At least one cDNA segment for each gene was found to contain the correct sequence. The segments containing the correct sequence will be used to replace the NS1 and M2 genes in the cDNA.

pBR 322 was used as the plasmid vector because large size inserts are more stable in this low copy number plasmid. DH10B cells (Life Technologies) were used to carry the functional BRSV cDNA clone.

EXAMPLE 4

Recovery and Characterization of Infectious BRSV from cDNA

The bovine turbinate (Btu) cells were chosen for transfection experiments because these cells are highly permissive for BRSV and vaccinia virus. In addition, these cells can be transfected efficiently by the LipofectACE method (Life Technologies). Initially, we will use the transfection condition that was used to rescue infectious HRSV (see Collins et al. *Proc. Natl. Acad. Sci. USA* 92: 11563–11567 (1995)). Briefly, confluent monolayers of Btu cells in six-well dishes are infected with 1 focus-forming unit per cell of recombinant vaccinia virus strain MVA that expresses T7 RNA polymerase (MVA-T7) (available from Dr. B. Moss, NIH, Bethesda, Md.). The MVA strain is a host-range mutant that grows permissively in avian cells, whereas in mammalian cells the virus expresses T7 RNA polymerase but there is no production of infectious virus due to a block at a late stage in virion maturation. A mixture of four plasmids containing the BRSV genes N, P, L, and M2 (ORFI) under the control of the T7 promoter (0.4, 0.4, 0.2 and 0.2 μg per well, respectively) and a fifth plasmid (i.e., p(+) BRSV)

encoding the functional BRSV antigenome (0.4 μg) is transfected with LipofectACE as recommended by the supplier (Life Technologies). Cells are incubated in a $CO_2$ incubator at 32° C. Twelve hours later, the medium is replaced with opti-MEM medium (Life Technologies) containing 2% FBS and 40 μg of cytosine arabinoside per ml to inhibit the replication of vaccinia virus. After 3 days, clarified medium supernatants are passaged onto fresh Btu cells and overlaid with methyl cellulose for staining with monospecific antibodies to BRSV F protein by the horseradish peroxidase method (see Murphy et al. *Vaccine* 8: 497–502) or 1% agarose for plaque isolation. Control transfections include cells that received the support plasmids but no p(+)BRSV, and cells that receive p(+)BRSV but no support plasmids. Different transfection conditions are tested to achieve the highest level of BRSV recovery. Several BRSV-like plaques are picked from plates that had been overlaid with agarose. Each plaque is further purified by two plaque to plaque isolations. Stocks of each plaque isolate are made in Btu cells for characterization. A schematic of the transfection procedure is shown in FIG. 12.

It will then be ascertained that the recovered virus is BRSV. A plaque neutralization test is performed using polyclonal antiserum raised against wild-type BRSV strain A59108. Methylcellulose overlay and neutral red staining is used in the plaque assay. Wild-type BRSV strain A59108 is used as a positive control and wild-type vaccinia virus is used as a negative control. The size of the plaques derived from recovered BRSV is compared with those of the wild-type BRSV strain A51908.

To verify that the three sequence markers inserted into the functional cDNA are present in the recovered BRSV, reverse transcription of genomic RNA purified from wild-type and recombinant BRSV using primers upstream of each restriction site is carried out. The reverse transcription products are amplified by PCR using an additional primer downstream of each restriction site. The presence of the sequence marker in the recombinant virus is verified by digestion of the PCR products with appropriate restriction enzymes. The PCR products representing the recombinant BRSV contains the expected restriction sites while those representing the wild-type BRSV do not contain the restriction sites. To further confirm the sequence markers, the PCR products are cloned and sequenced. This confirms that the recovered BRSV is produced from cDNA clones and is not a laboratory contamination of wild-type BRSV.

The replication behavior of the recovered BRSV is thereafter compared with that of the wild-type BRSV strain A51908. Briefly, Btu cell monolayers in 25 $cm^2$ culture flasks are infected with 2 PFU of either virus per cell. One flask every 12 hours is transferred to −70° C. The samples are subsequently thawed and titrated in parallel by plaque assay. Only 2 PFU of BRSV per cell are used because BRSV does not grow to high titer. This study indicates any difference in the replication behavior between the recombinant and wild-type BRSV.

To compare the proteins synthesized by the recombinant BRSV with those of the wild-type BRSV, Btu cells are infected with recombinant BRSV or wild-type BRSV strain A51908 at a multiplicity of infection of 2 PFU. At 20 hours postinfection, the infected cells are labeled with $^{35}S$ methionine for 2 hours (see Mallipeddi et al. *Arch. Virol.* 115: 23–36 (1990)). The labeled cells are washed with PBS and lysed in radioimmunoprecipitation assay (RIPA) buffer. The lysates are clarified by centrifugation and stored at −70° C. An aliquot of each lysate is immunoprecipitated by a BRSV-specific polyclonal antiserum (see Mallipeddi et al., supra). Total infected cell lysates and immunoprecipitated complexes are analyzed by electrophoresis in 12% polyacrylamide gels. The mobilities and relative amounts of the BRSV proteins are compared between the two viruses.

EXAMPLE 5

Construction of P Gene Mutants

To define regions of the BRSV P protein important for transcription, replication, and the formation of protein complexes, a panel of 39 P mutants representing 22 different deletions, or 17 different single or double amino acid substitutions was made. In one set of deletion mutations, a segment of 20 amino acids in length was deleted at intervals of 20 amino acids, spanning the entire 241-amino-acid protein. A second set of deletion mutations was constructed in which 1, 2, 3, 4, 8, or 13 amino acids were deleted from either the N- or the C-terminus.

One set of substitution mutations was designed to individually change amino acids 2, 3, and 4 at the N-terminus to alanine. In addition, single or double substitutions to alanine were made involving every residue of the C-terminal 13 amino acids of P (residues 229–241). The activity of these P protein mutants in transcription and replication was analyzed.

To examine expression of these mutant proteins, HEp-2 cells were transfected with either wild-type or mutant pTM1-P plasmid together with the pTM1-N and pTM 1-L support plasmids and infected with a recombinant of the modified vaccinia virus strain Ankara that expresses T7 RNA polymerase (MVA-T7), as described below. Expression of the wild-type or mutant P proteins containing the various deletions was determined by Western blot analysis. As described later, expression of the mutants containing amino acid substitutions was examined by immunoprecipitation. Each of the deletion and substitution P mutant proteins accumulated intracellularly to a level comparable to that of wild-type P protein; thus, the effects described later were not due to differences in expression nor to stability of various mutant P proteins.

The ability of the various P protein mutants to participate in transcription of a previously described negative-sense BRSV minigenome, BLT delta 7, containing the full-length CAT gene was evaluated. The plasmid encoding BLT delta 7 was cotransfected with the N, P, and L support plasmids into cells infected with the MVA-T7 virus (Yunus et al., *J. Gen. Virol.* 79: 2231–2238 (1998)). These conditions reconstitute BRSV-mediated transcription and replication of the plasmid-encoded minigenome. Cells were harvested at 48 h posttransfection, and lysates were prepared and subjected to CAT assay to monitor gene expression.

Minigenome transcription and RNA replication was also monitored by purifying total intracellular RNA and subjecting it to Northern blot analysis using a negative-sense CAT-specific RNA probe. The experiments involving RNA analysis employed a minigenome designed to express a shortened version of the CAT mRNA that could be readily separated electrophoretically from the antigenomic RNA. Specifically, the BLT delta 7 construct was modified to produce the SK 7 construct, by insertion of a BRSV consensus gene-end motif at the BspEI site in the CAT OAF, such that transcription yielded a truncated CAT mRNA of 274 nucleotides, compared to the antigenomic RNA of 955 nucleotides (Khattar et al., supra). In all of the minigenome experiments, there was a very close correlation between the level of CAT activity and the accumulation of positive-sense mRNA encoded by the plasmid-supplied minigenome. As described below, the P protein mutations could be classified into four categories based on their level of expression of CAT enzyme and mRNA relative to the wild-type: (I) 50–100% expression; (II) 20–50% expression; (III) 2–20% expression; and (IV) <2% expression.

Twelve internal deletions of 20 amino acids each were made throughout the 241-amino-acid P protein (SEQ ID NO: 16) (mutants PΔ1–20, PΔ21–40, PΔ41–60, PΔ61–80, PΔ81–100, PΔ101–120, PΔ121–140, PΔ141–160, PΔ161–180, PΔ181–200, PΔ201–220, and PΔ221–241). Deletion of 20 amino acids at the N-terminal (mutant PΔ1–20), and any deletion in the region of amino acids 101–241, completely inhibited (<2% expression) P protein expression as revealed by CAT expression and mRNA synthesis. Deletion of amino acids 21–40 or 81–100 drastically reduced CAT activity and mRNA synthesis (2–20% expression), whereas deletion of amino acids 61–80 resulted in a moderate reduction (20–50% expression). Deletion of amino acids 41–60 (SEQ ID NO: 18) of the P protein increased the CAT activity and mRNA synthesis by nearly twofold. These results suggest that a region within amino acids 41–60 in the P protein contains sequences that negatively regulate transcription.

A second set of mutants contained a series of small deletions at the N- and C-terminal ends of the P protein. Removal of 1, 2, or 3 amino acids from the N-terminus had a moderate effect on expression, whereas removal of 4 or 8 amino acids from the N-terminus greatly reduced or completely ablated CAT expression and mRNA synthesis. Removal of 1 or 3 amino acids from the C-terminus had a moderate effect, whereas removal of 4 or 8 amino acids had a drastic effect on CAT activity and mRNA synthesis. Removal of 13 amino acids from the C-terminus completely inhibited P protein function.

Substitution mutations involving the conserved glutamic acid, lysine, and phenylalanine residues present at positions 2 (mutant E 1 A), 3 (mutant K2A), and 4 (mutant F3A), respectively, of the N-terminus were evaluated for CAT expression and mRNA synthesis. At position 2, the change of glutamic acid to alanine was completely inhibitory, whereas, at positions 3 and 4, the changes of lysine and phenylalanine to alanine reduced minigenome transcription by 4-and 16-fold, respectively.

The remaining P protein mutations involved single or double substitutions within residues 229–241 at the C-terminus. Mutation of the potential phosphorylation sites at S231, S232. S237, or S232 and S237 together had little or no effect on CAT expression or mRNA synthesis. Within the 13-amino-acid sequence of positions 229–241, two substitutions, namely D229A and D240A, reduced transcription by 3-and 10-fold, respectively, and four substitutions, namely N234A. L236A, L238A, and F241A, completely ablated transcription.

The ability of the mutant P proteins to support RNA replication was also examined. All the internal deletions except PΔ41–60 and PΔ61–80 were inactive in anti-genome synthesis. Deletion of amino acids 61–80 reduced anti-genome synthesis by twofold, whereas deletion of amino acids 41–60 increased anti-genome synthesis by approximately twofold. Thus, the effects of these mutations on the synthesis of antigenomic RNA appeared to be the same as for transcription. In particular, the region which appeared to negatively regulate transcription had a similar effect on replication. Similarly, substitution mutations in the C-terminal region of P had similar effects on the synthesis of antigenomic RNA and mRNA Specifically, substitutions at N234, L236. L238, D240, and F241 were highly inhibitory, whereas the other substitutions were well tolerated, including those at the potential phosphorylation sites S231, S232, and S237. In contrast, a number of other types of mutations severely inhibited the synthesis of antigenomic RNA while permitting a substantial level of transcription. For example, deletion of one, two, or three amino acids from the N-terminus completely ablated the synthesis of antigenomic RNA, while up to 43% of transcription remained. Similarly, deletions of up to three or four amino acids from the C-terminus, or substitution at position 3 (mutant K2A), completely ablated the synthesis of antigenomic RNA while leaving substantial residual transcription.

The ability of P protein mutants to support the synthesis of negative-sense minigenomic RNA in the reconstituted system was examined. In this reconstituted system, minigenomic RNA is synthesized directly from the transfected plasmid by T7 RNA polymerase, encapsidated by plasmid-supplied nucleocapsid proteins, and replicated by the reconstituted BRSV polymerase. Therefore, it was necessary to reduce the background of plasmid-derived minigenomic RNA in order to visualize the one that was amplified by the BRSV polymerase. This was done by lysing the harvested cells with nonionic detergent followed by treatment with micrococcal nuclease (MCN) to destroy unencapsidated RNA. The remaining RNAs were purified and analyzed by Northern blotting with a positive-sense CAT RNA probe. Under these conditions, a background of genomic RNA was detected in the absence of BRSV polymerase, representing encapsidated plasmid-derived RNA as well as a possible small amount of undegraded, unencapsidated, plasmid-derived RNA. The amount of material in the genomic RNA band was greatly increased in the presence of the complete polymerase, indicating the extent of amplification mediated by the reconstituted BRSV polymerase. The effects of the various mutations on the synthesis of genomic RNA paralleled the effects described above for antigenomic RNA. For example, all of the deletions of 20 amino acids within the body of the P protein were highly inhibitory except for PΔ61–80, which reduced synthesis threefold, and PΔ41–60, which increased synthesis approximately twofold. Similarly, substitutions within the C-terminal 13 amino acids that were inhibitory to the synthesis of antigenomic RNA (and transcription) also were inhibitory to the synthesis of genomic RNA, such as N234A, L236A. L238A, and F241A, whereas substitutions within this region that were not inhibitory, or were partially inhibitory, to the synthesis of antigenomic RNA (or transcription) had the same effect on the synthesis of genomic RNA, as exemplified by two- to threefold inhibition associated with D229A. Finally, the mutations in the N- or C-terminus that inhibited the synthesis of antigenomic RNA, but left substantial residual transcription, also inhibited the synthesis of genomic RNA, such as PCΔ1 and PNΔ1.

Materials and Methods i. Cells, Viruses and Antiserum

HEp-2 and bovine turbinate (Btu) cells were grown in Eagle's minimal essential medium (EMEM) supplemented with 5% fetal bovine serum. Strain A51908 of BRSV was propagated in Btu cells. Modified vaccinia virus strain Ankara (MVA) expressing T7 RNA polymerase was propagated in chick embryo fibroblast cells (Wyatt et al., *Virology* 210: 202–205 (1995)). HEp-2 cells, grown in six-well culture dishes (35-mm-diameter plates), were used for transfections. For coimmunoprecipitation studies, monospecific serum raised against *Escherichia coli*-expressed P protein was used.

ii. Plasmids and the Mutants of P Gene

Plasmids pTM1-P, pTM1-N, and pTM1-L containing the BRSV P, N, and L genes (A51908 strain), respectively, cloned downstream of the T7 RNA polymerase promoter of plasmid pTM-1, have been described previously (Yunus et al., supra). Construction of the BRSV minigenome BLT delta 7 has been described previously (Id.). Briefly, the BLT delta 7 minigenome contains a negative-sense copy of the bacterial CAT gene under the control of BRSV genestart and gene-end (GE) transcription signals and flanked by the leader and trailer regions of BRSV genomic RNA. Its 3' end is generated by a self-cleaving ribozyme from the anti-genome strand of hepatitis delta virus. Construction of the BRSV mlnigenome SK 7 has been described previously (Khattar et al., supra). Briefly, the cDNA encoding minigenome SK 7 was constructed from BLT delta 7 cDNA by insertion into a unique BspEI site within the CAT sequence of a synthetic DNA containing a consensus GE motif of BRSV. This GE insertion resulted in !he synthesis of a subgenic CAT mRNA of 274 nt by the SK 7 minigenome construct, compared to 745 nt CAT mRNA synthesized by the BLT delta 7 construct. The 274-nt subgenic positive-sense CAT mRNA encoded by SK7 could be easily distinguished from the 955-nt BRSV- CAT positive-sense anti-genome after electrophoresis on formaldehyde-1.5% agarose gels.

Site-specific point mutations and amino- and carboxy-terminal and internal deletions of the P gene of BRSV were carried out by a single round of PCR, using the method described by Byrappa et al., supra. Briefly, 21-mer primers were phosphorylated at their 5' ends using T4 polynucleotide kinase (New England Biolabs) at 37° C. for 1 h. Twenty-five picomoles of each phosphorylated internal primer pair was used to amplify 20 ng of plasmid DNA. Fourteen cycles of PCR amplifications were carried out with Pfu Turbo DNA polymerase (Stratagene) (1 min at 94° C., 1 min at 55° C., and 6.5 min at 72° C.). All P gene mutants were sequenced in their entirety and confirmed for correct P protein expression by in vitro transcription and translation, using the rabbit reticulocyte lysate system as described by the supplier (Promega).

iii. Transfections

Transfections were performed as described by Grosfeld et al., *J. Virol.* 69: 5677–5686 (1995). Briefly, HEp-2 monolayers in six-well plates were infected with MVA- T7 at an m.o.i. of 5 PFU per cell and transfected with the following mixture of plasmids per single well by using Lipofectamine Plus reagent and Lipofectamine, as described by the supplier (Life Technologies): 0.4 $\mu$g of either BLT delta 7 minigenome or SK 7 minigenome DNA; 0.2 $\mu$g of either wild-type or mutant pTM1-P; 0.4 $\mu$g of pTM1-N; and 0.1 $\mu$g of pTM 1-L. Five hours later, the transfection medium was replaced with EMEM containing 10% fetal bovine serum. Depending on the specific experiment, cells were harvested at 48 h posttransfection and processed for Western blot analysis, CAT activity, or Northern blot analysis or radiolabeled at 24 h posttransfection for immunoprecipitation of proteins.

iv. CAT Assay

Cell pellets from individual wells transfected with BLT delta 7 minigenome cDNA and all the support plasmids were harvested by scraping, separated into two identical aliquots, and pelleted by centrifugation. One of the aliquots was resuspended in sodium dodecyl sulfate (SDS) sample buffer and analyzed by Western blotting with P-specific antiserum. The other aliquot was resuspended in 200 $\mu$l of 0.25 M Tris-HCl (pH 7.5), lysed by three cycles of freezing and thawing, and clarified by brief centrifugation in a microcentrifuge. Aliquots of the clarified supernatant were used to determine the total protein content (with a Pierce protein assay kit), the CAT activity, using D-threo-[dichloroacetyl-1-$^{14}$C]chloramphenicol (50 to 60 mCi/mmol) (Amersham) as the substrate, according to the standard procedure (Gorman et al. *Mol. Cell. Bio.* 2: 1044–1051 (1982)). Different amounts (3 to 20 $\mu$l) of the cell extracts were incubated with radioactive chloramphenicol for 2 h to obtain CAT activity values in the linear range. Quantitation of the CAT activity was done by liquid scintillation counting of excised spots. The values obtained were corrected for the protein concentration of the cell extract and were expressed as a percentage of the CAT activity observed for cells expressing the wild-type P protein.

v. Western Blot Analysis

One half of the volume of the total cells harvested from one well was lysed in a SDS-polyacrylamide gel electrophoresis sample buffer containing β-mercaptoethanol, and lysate representing about 1/20th of one well of cells was subjected to electrophoresis through a 4–20% gradient gel, and the separated polypeptides were transferred to nitrocellulose, using conventional techniques. BRSV-specific wild-type or mutant P proteins were detected by incubation with P-specific antiserum, followed by incubation with horseradish peroxidase-labeled goat anti-rabbit IgG (Kirkgaard and Perry Laboratories), followed by peroxidase reaction using 1 component of TMB membrane peroxidase substrate (Kirkgaard and Perry Laboratories).

vi. RNA Isolation and Northern Blot Analysis

Cell pellets from individual wells transfected with SK 7 minigenome cDNA and all the support plasmids were harvested by scraping, separated into two identical aliquots, and pelleted by centrifugation. One of the aliquots was used for extraction of total intracellular RNA for Northern blot analysis. The other aliquot was subjected to micrococcal nuclease digestion before RNA extraction and Northern blot analysis. RNA was isolated with TRIzol reagent according to the supplier's protocol. Depending on the specific experiment, one-third of the total intracellular RNA, either undigested or micrococcal nuclease digested (approximately 5–10 $\mu$g, representing one-sixth of the total amount from each well), was electrophoresed on 0.44 M formaldehyde, 1.5% agarose gel and transferred to nylon membrane. The RNAs were fixed at 80° C. for 1 h. Prehybridization was performed for 6 h at 65° C. with prehyb/hyb buffer (Quality Biologicals) containing 6×SSG, 5×Denhardt's solution, 0.5% SDS, and 0.5 mg/ml sheared salmon sperm DNA. Hybridization was performed overnight under the same conditions with approximately 2×10$^6$ dpm of positive-sense or negative-sense strand-specific CAT riboprobe. To synthesize these probes, a 672-bp CAT gene, derived from PstI-XbaI-digested BLT delta 7, was subcloned in pGEM-4Z vector (Promega), generating plasmid pGEM4Z-CAT. Negative- or positive-sense CAT riboprobes were synthesized by in vitro transcription of XbaI- or PstI-digested pGEMZ-CAT DNA. The densitometric analysis of autoradiographs of Northern blots was carried out using a densitometer (Molecular Dynamics).

vii. Micrococcal Nuclease Protection Assay

To identify encapsidated RNA, MCN protection assay was done according to Baker and Moyer, *J. Virol.* 62: 834–838 (1988). Briefly, one-half of the cell pellet from one 35-mm well transfected with SK 7 minigenome cDNA and all the support plasmids was disrupted in 50 $\mu$l of RSB (10 mM NaCl. 10 mM Tris, pH 7.5, 1.5 mM MgCl2)-1.0%

Triton X-10O-0.5% DOC-aprotinin. The clarified cytoplasmic extract (3000 g for 15 min at 4° C.), supplemented with 50 μl of Tris-$CaCl_2$ buffer (10 mM Tris, pH 7.5, 2 mM $CaCl_2$), was incubated with 6 units of MCN (Roche Molecular Biochemicals) for 30 min at 30° C. The RNA was extracted as described above.

viii. Radiolabeling of Cells and Immunoprecipitation

Twenty-four hours after transfection or infection, the cells were washed and incubated in methionine-free EMEM for 2 h before labeling with [$^{35}$S]methionine (100 μCi/ml). After 4–8 h of labeling, the cells were harvested. The cells were lysed in a buffer containing 50 mM Tris-HCI (pH 7.5), 150 mM NaCl, and 0.7% Nonidet P-40. Nuclei were eliminated from the lysate by centrifugation at 10,000 rpm for 15 min at 4° C. The cytoplasmic fractions were incubated overnight at 4° C. with antibodies (P-specific antiserum, which is preadsorbed with MVA-infected HEp-2 cell lysate). Formalin-fixed killed Staph A cells (Gibco BRL), resuspended in 100 mM NaCl-10 mM Tris, pH 7.5–1 mM EDTA-1% BSA, were added to the lysate and incubated at 4° C. for 2 h. The Staph A cells were pelleted, and supernatants were removed. The pellets were washed once with Salt Wash A buffer (1.0 M NaCl, 0.01 M Tris-HCl, pH 7.2, 0.1% vol/vol NP-40) and two times with Salt Wash C buffer (0.01 M Tris-HCl, pH 7.2. 0.1% vol/vol NP40). The Staph A cells were then resuspended in a sample buffer and analyzed by SDS-polyacrylamide gel electrophoresis. Samples were incubated at 100° C. for 5 min prior to loading on SDS-12% polyacrylamide gel. Densitometric analysis of autoradiographs of polyacrylamide gels was carried out using a densitometer (Molecular Dynamics).

I claim:

1. A method of producing an attenuated bovine respiratory syncytial virus (BRSV) having increased or decreased transcription and/or replication, as compared to a wild-type BRSV, the method comprising inserting a synthetic cDNA which codes for an infectious BRSV comprising a phosphoprotein (P) gene, into a host cell, wherein the cDNA is operably-linked to a promoter; expressing the cDNA in the host cell to produce the infectious BRSV; and thereafter introducing at least one site-specific RNA point mutation on the P gene to produce an attenuated BRSV having increased or decreased transcription and/or replication, as compared to a wild-type BRSV.

2. The method of claim 1, further comprising purifying the attenuated BRSV.

3. The method of claim 1, wherein the cDNA is derived from a single strain of BRSV.

4. The method of claim 1, wherein the cDNA is a chimeric cDNA which is derived from more than one strain of BRSV.

5. The method of claim 1, wherein the at least one site-specific RNA point mutation on the P gene is made on SEQ ID NO:17 to produce an attenuated BRSV having increased transcription and/or replication, as compared to a wild-type BRSV.

6. The method of claim 1, wherein at least one site-specific RNA deletion is made on the P gene.

7. The method of claim 1, wherein at least one site-specific RNA substitution is made on the P gene.

8. The method of claim 1, wherein at least one site-specific RNA deletion is made on SEQ ID NO: 17 to produce an attenuated BRSV having increased transcription and/or replication, as compared to a wild-type BRSV.

9. The method of claim 1, wherein at least one site-specific RNA substitution is made on SEQ ID NO: 17 to produce an attenuated BRSV having increased transcription and/or replication, as compared to a wild-type BRSV.

10. The method of claim 5, wherein the attenuated BRSV has at least 1.5 times increased transcription and/or replication, as compared to a wild-type BRSV.

11. The method of claim 5, wherein the attenuated BRSV has at least two times increased transcription and/or replication, as compared to a wild-type BRSV.

12. An attenuated BRSV, produced by the method of claim 1.

13. A vaccine, comprising an attenuated BRSV according to claim 12, in combination with a pharmaceutically acceptable carrier.

* * * * *